US012614619B2

(12) United States Patent
Thompson et al.

(10) Patent No.: US 12,614,619 B2
(45) Date of Patent: Apr. 28, 2026

(54) MONITORING AND OPTIMIZATION OF HUMAN-DEVICE INTERACTIONS

(71) Applicants: Benjamin Simon Thompson, Wellesley (CA); Robert Francis Hess, Montreal (CA); Otman Basir, Waterloo (CA); Anoop Thazhathumanackal Radhakrishnan, Waterloo (CA)

(72) Inventors: Benjamin Simon Thompson, Wellesley (CA); Robert Francis Hess, Montreal (CA); Otman Basir, Waterloo (CA); Anoop Thazhathumanackal Radhakrishnan, Waterloo (CA)

( * ) Notice: Subject to any disclaimer, the term of this patent is extended or adjusted under 35 U.S.C. 154(b) by 50 days.

(21) Appl. No.: 18/690,526

(22) PCT Filed: Sep. 13, 2022

(86) PCT No.: PCT/IB2022/058632
§ 371 (c)(1),
(2) Date: Mar. 8, 2024

(87) PCT Pub. No.: WO2023/037348
PCT Pub. Date: Mar. 16, 2023

(65) Prior Publication Data
US 2024/0379206 A1 Nov. 14, 2024

Related U.S. Application Data

(60) Provisional application No. 63/243,612, filed on Sep. 13, 2021.

(51) Int. Cl.
*G16H 20/00* (2018.01)
*G06V 40/16* (2022.01)
(Continued)

(52) U.S. Cl.
CPC ............. *G16H 20/00* (2018.01); *G06V 40/16* (2022.01); *G06V 40/18* (2022.01); *G08B 21/06* (2013.01)

(58) Field of Classification Search
None
See application file for complete search history.

(56) References Cited

U.S. PATENT DOCUMENTS 6,927,694 B1    8/2005   Smith et al.
9,436,984 B2    9/2016   Xu et al.
(Continued)

FOREIGN PATENT DOCUMENTS

CN       111179551 A   *   5/2020   .......... G08B 25/006

OTHER PUBLICATIONS

C. Ahlstrom, K. Kircher and A. Kircher, "A Gaze-Based Driver Distraction Warning System and its Effect on Visual Behavior," in IEEE Transactions on Intelligent Transportation Systems, vol. 14, No. 2, pp. 965-973, Jun. 2013. (Year: 2013).*
(Continued)

*Primary Examiner* — Robert A Sorey

(57) ABSTRACT

A real time system for monitoring and optimizing patient adherence to digital therapy. The system can measure at least one of head stability, eye stability, gaze direction, head pose, facial expression, reading related eye movements, eye alignment stability, eye blink rate, attentive engagement, general engagement, emotional state, total eye stability, yawning and distance between the user and the camera. This information is provided as input to computer vision algorithms to generate a multi-dimensional representation of user attention and engagement. The system can alert the caregiver or health care professional if the patient disengages from the treatment and if the patient is sitting at the wrong distance from the treatment device. The system includes a camera, a
(Continued)

processor, computer vision algorithms executed by the processor (a GPU processor), at least one digital display device, a loud speaker and an optional internet connection that can enable communication with other electronic devices.

16 Claims, 32 Drawing Sheets

(51) Int. Cl.
    *G06V 40/18*         (2022.01)
    *G08B 21/06*         (2006.01)

(56)           References Cited

U.S. PATENT DOCUMENTS

| | | | |
|---|---|---|---|
| 9,706,910 B1 | 7/2017 | Blaha et al. | |
| 10,357,195 B2 | 7/2019 | Beck et al. | |
| 11,315,350 B2 | 4/2022 | Wu et al. | |
| 2003/0151516 A1* | 8/2003 | Basir | G08B 21/06 |
| | | | 600/300 |
| 2004/0220705 A1* | 11/2004 | Basir | G01S 3/786 |
| | | | 701/1 |
| 2016/0001781 A1* | 1/2016 | Fung | G07C 9/37 |
| | | | 701/36 |
| 2017/0247037 A1* | 8/2017 | Basir | G09B 19/14 |
| 2019/0111945 A1* | 4/2019 | Wiegand | B60K 35/231 |
| 2022/0001893 A1* | 1/2022 | Tartz | A61B 5/02055 |

OTHER PUBLICATIONS

Arriaga et al., "Real-time Convolutional Neural Networks for Emotion and Gender Classification" arXiv:1710.07557v1 [cs.CV] Oct. 20, 2017.
Bergasa et al., IEEE Transactions on Intelligent Transportation Systems, vol. 7, No. 1, pp. 63-77, Mar. 2006.
Chollet, Francois, "Xception: Deep learning with depthwise separable convolutions" CoRR, abs/1610.02357, 2016.
Chow et al. (2021). "Efficacy of vision-based treatments for children and teens with amblyopia: a systematic review and meta-analysis of randomized controlled trials" BMJ Open Ophthalmology, 6, e000657.
Davoudi et al., "Intelligent ICU for Autonomous Patient Monitoring Using Pervasive Sensing and Deep Learning" 2019, 9:8020 | https://doi.org/10.1038/s41598-019-44004-w.
Gao et al. (2018). Effectiveness of a binocular video game vs placebo video game for improving visual functions in older children, teenagers and adults with amblyopia. A randomized clinical trial. JAMA Ophthalmology, 136(2), 172-181.
Gao et al.(2021), Adherence to home-based videogame treatment for amblyopia in children and adults. Clinical and Experimental Optometry, online ahead of print. doi: 10.1080/08164622.2021. 1878834.
Hess et al. (2015). "Amblyopia and the binocular approach to its therapy" Vision Research, 114, 4-16.
Ji et al., "Real-Time Nonintrusive Monitoring and Prediction of Driver Fatigue," IEEE Transactions on Vehicular Technology, vol. 53, No. 4, pp. 1052-1068, 2004.
Kar et al., "A Review and Analysis of Eye-Gaze Estimation Systems, Algorithms and Performance Evaluation Methods in Consumer Platforms", vol. 5, 2017, DOI 10.1109/ACCESS.2017. 2735633.
Kazemi et al., One millisecond face alignment with an ensemble of regression trees. In Proceedings of the IEEE Conference on Computer Vision and Pattern Recognition, Columbus, OH, USA, Jun. 23-28, 2014; pp. 1867-1874.
Li et al. (2013). Dichoptic training enables the amblyopic brain to learn. Current Biology, 23(8), R308-9.
Pimplaskar et al., "Real Time Eye Blinking Detection and Tracking Using Opencv" Int. Journal of Engineering Research and Application www.ijera.com ISSN : 2248-9622, vol. 3, Issue 5, Sep.-Oct. 2013, pp. 1780-1787.
Schwarz et al. (2019) The detection of drowsiness using a driver monitoring system, Traffic Injury Prevention, 20: sup1, S157-S161, DOI: 10.1080/15389588.2019.1622005.
Simonsz et al., "Electronic monitoring of treatment compliance in patching for amblyopia" Journal Strabismus vol. 7, 1999—Issue 2.
Wu et al., "Gaze direction estimation using support vector machine with active appearance model," Multimed. Tools Appl., pp. 1-26, 2012.
International Search Report and Written Opinion issued in corresponding international application No. PCT/IB2022/058632 dated Jan. 18, 2023.

* cited by examiner

frame_iris_track_3
07
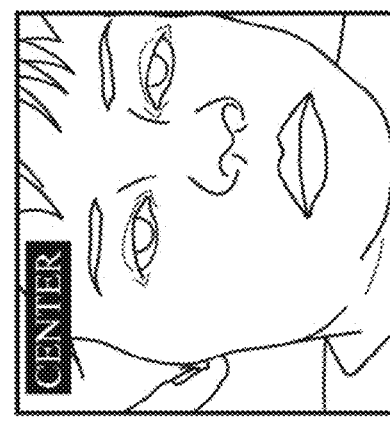
frame_iris_track_3
10
frame_iris_track_3
06
frame_iris_track_3
09
FIG. 8
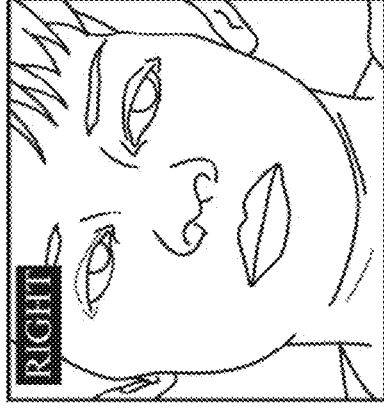
frame_iris_track_3
05
frame_iris_track_3
08

MONITORING AND OPTIMIZATION OF HUMAN-DEVICE INTERACTIONS

CROSS REFERENCE TO RELATED APPLICATIONS

This application claims the benefit of priority of U.S. Provisional Patent Application No. 63/243,612 filed Sep. 13, 2021, which is hereby incorporated by reference.

FIELD

The present disclosure relates generally to monitoring the attentional and emotional state of a machine-operator or digital treatment recipient and providing feedback to optimize attention and engagement.

BACKGROUND

Human-device interactions take many forms and include activities such as using a computer system, controlling vehicles, and operating machinery. Optimal human-device interactions typically require sustained attention and engagement from the device user. One specific example is the case of digital therapeutics whereby digital devices such as computers, tablets, virtual reality systems or smart phones are used to deliver treatment for a particular medical condition, typically within the home. For instance, modified videogames and movies have been used to treat a neuro developmental disorder of vision known as amblyopia. Individuals with amblyopia experience reduced vision in one eye and suppression (blocking of information from the affected amblyopic eye from conscious awareness when both eyes are open) caused by abnormal development of visual processing within the brain. One type of known digital therapy for amblyopia involves presenting some elements of a videogame or movie to the amblyopic eye at a high contrast (high visibility) and the remaining elements to the non-amblyopic eye at low contrast (low visibility). This "contrast balancing" approach enables the brain to process information from both eyes simultaneously. Another known technique is dichoptic presentation of images/video via specialized screens, such as for example auto-stereoscopic screens, lenticular screens or other screens that do not require the person viewing to wear special glasses such as red-green glasses.

In past controlled laboratory studies, exposure to contrast balanced games or movies improved vision in patients with amblyopia. However, a home-based treatment for patients with amblyopia may have a reduced or no effect by the treatment. A detailed analysis of the device-based treatment adherence data that was stored on a device used by a patient in a home environment was conducted. The treatment adherence data included simple human-device interaction metrics including duration and frequency of game play, frequency of pauses, cumulative play time, time of day that play occurred and game performance. The analysis revealed poor adherence and frequent disengagement from the treatment in the home environment. It is likely that distractions in the home environment are the cause of this. This is an example of a failed human-device interaction and an indication of the need for attention and engagement during human device interactions. Other examples include driver or pilot fatigue causing an accident and a pupil disengaging from an online class and failing to meet the associated learning objectives.

Previous approaches to monitoring human-device interactions have recorded device-based metrics such as the duration, timing, and frequency of the interactions for offline analysis. However, this approach is insufficient because direct measures of the user's level of engagement and attention are required. The following scenario illustrates this point. A patient at home is provided with a specially developed dichoptic video game designed to treat amblyopia, is played on a digital device over multiple days at the prescribed dose. Adherence to the prescribed dose is confirmed by measures of game presentation time, game-play duration and game performance recorded on the presentation device. However, the effect of the video was diminished because the patient frequently looked away from the device screen to watch a television program. The frequent disengagement from the game, that was not captured by the device-based adherence metrics, made the treatment less effective. Optimization of human device interactions using real-time feedback also requires inputs that go beyond device-based metrics and directly quantify and assess biomarkers of user engagement and attention.

Monitoring systems developed for digital treatments such as the amblyopia treatment described above have relied solely on device-based metrics or direct monitoring of the patient by another human.

The traditional treatment for amblyopia involves using an eye-patch to occlude the non-amblyopic eye. An occlusion dose monitor (ODM) has been developed to objectively measure compliance with patch-wearing during the treatment of amblyopia. A magnet-based monitoring system has also been developed for the occlusion-based treatment of amblyopia. This system uses two magnetometers connected to a microcontroller for the measurement of the local magnetic field. An interactive occlusion system, including software and hardware, has also been developed for the treatment of amblyopia. This system precisely records patient's occlusion compliance and usage time during occlusive and non-occlusive periods. It also measures the patient's visual acuity as well as the capacity for entering prescriptions and treatment plans for individual patients. An electronically controlled, liquid-crystal eyeglass system for intermittent amblyopic eye occlusion that consists of the electronic components in miniaturized and hidden form has also been developed. These solutions are specific to occlusion therapy for amblyopia and cannot be applied to other human-device interaction scenarios including digital therapies for amblyopia.

A head-mountable virtual reality display for correcting vision problems controlled via a computing device that can be worn by a user to display virtual reality images has been developed. It acquires the input from at least one sensor selected from a group consisting of a head tracking sensor, a face tracking sensor, a hand tracking sensor, an eye tracking sensor, a body tracking sensor, a voice recognition sensor, a heart rate sensor, a skin capacitance sensor, an electrocardiogram sensor, a brain activity sensor, a geo location sensor, at least one retinal camera, a balance tracking sensor, a body temperature sensor, a blood pressure monitor, and a respiratory rate monitor to determine the user's perception of the displayed virtual reality images. However, this system is limited by modality-specific sensors (i.e. sensors that only detect one element of the human-device interaction such as heart rate) and it does nothing to help optimize the human-device interaction.

Patient monitoring systems for more general use in healthcare settings may be sensor based or a combination of video and sensor based or video-based systems. Prior patents on patient monitoring systems have utilized a variety of different inputs. For example, a patient monitoring system based on deep learning developed for the ICU uses wearable sensors, light and sound sensors, and a camera to collect data on patients and their environment. Driver monitoring systems (DMS) have used a camera to detect eye blinking, eye gaze and head poses to determine the state of the driver and trigger an alarm if drowsiness or disengagement is detected. A model for DMS has been developed that uses the fusion of information from an external sensor and an internal camera to detect drowsiness. A real-time system for nonintrusive monitoring and prediction of driver fatigue using eyelid movement, gaze movement, head movement, and yawning has also been described. A method and system that uses emotion trajectory to detect changes in emotional state along with gaze direction estimated from eye position and three-dimensional facial pose data has been developed to measure the emotional and attentional response of a person to dynamic digital media content.

The methods described above have used eye gaze, eyelid closure, face orientation and facial expressions like yawning for driver monitoring and patient monitoring purposes. However, they have not combined these parameters to generate a multi-dimensional system for human-device monitoring and optimization. In addition, the systems described above that include a feedback component primarily focus on warning the user or caregiver about a potentially dangerous situation rather than optimizing a human-device interaction.

It is, therefore, desirable to provide a system that monitors and, by feedback, improves human-device interactions.

SUMMARY

It is an object of the present disclosure to obviate or mitigate at least one disadvantage of previous systems that monitor and improve human-device interactions.

In one embodiment there is a real time system for monitoring and optimizing patient adherence to digital therapy. The system can detect patient behavior relating to treatment engagement and attention and modify the treatment in real-time to optimize engagement and attention. The system can also alert the caregiver or health care professional if the patient disengages from the treatment or if the patient is not wearing essential components necessary for the treatment such as anaglyph glasses or physical sensors and if the patient is sitting at the wrong distance from the treatment device. An alert can also be generated if someone other than the patient engages with the digital therapy. The system includes a camera, a processor, computer vision algorithms executed by the processor (a GPU processor), at least one digital display device, a loud speaker and an optional internet connection that can enable communication with other electronic devices. For example, such physical components are commonly found and integrated together into a tablet device. Alternately, such components do not have to be integrated together in a single device, but can be implemented as discrete devices with some of the components integrated together.

In the present embodiments, the system can measure at least one of head stability, eye stability, gaze direction, head pose, facial expression, reading related eye movements, eye alignment stability, eye blink rate, attentive engagement, general engagement, emotional state, total eye stability, yawning and distance between the user and the camera from each captured video frame. This information is provided as input to computer vision algorithms to generate a multi-dimensional representation of user attention and engagement.

According to an alternate embodiment, the real time system can be configured for monitoring students during online learning and providing alerts to the parent or teacher if one or more students are not attending the class. The system can also provide detailed analytics of attention and engagement using a version of the above mentioned computer vision algorithms during lessons that can be used to assess teacher performance and/or optimize lesson delivery.

In another embodiment the real time system is configured for strabismus classification.

In another embodiment the real time system for driver distraction/emotional state monitoring with feedback control to ensure corrective strategies, comprising a camera, GPU based processor and a feedback module.

In a first aspect, the present disclosure provides a real-time attention monitoring system. The system includes a screen at which a person's eyes are directed at, an image capture device, a computing device, and an audio output device. The image capture device is positioned to capture video frames of the person's head and face. The computing device is configured to receive the captured video frames and extract at least one visual cue of the person's head and face from each of the captured video frames. The computing device is further configured to analyse the at least one visual cue to measure and quantify at least one parameter for comparison to corresponding predetermined ranges, where the corresponding predetermined ranges represent a correct level of attention by the person; to detect the quantified at least one parameter falling outside of the corresponding predetermined range; and to generate at least one feedback indicating the person is disengaged with the screen when the at least one quantified parameter is detected to fall outside of the corresponding predetermined range. The audio output device is controlled by the computing device to provide audio signals to the person.

According to embodiments of the first aspect, the screen is an electronic display device controlled by the computing device for presenting preset graphics, images or videos for viewing by the person. Furthermore, the computing device is configured to detect from the captured video frames the at least one visual cue of eye gaze direction, rate of eye blinking and rate of yawning, and to measure and quantify their corresponding parameters. The computing device can be further configured to detect from the captured video frames the at least one visual cue of emotional state of the person as being one of happy, neutral, sad or angry. Furthermore, the computing device can be configured to determine a drowsy state of the person when the rate of eye blinking exceeds a predetermined blinking rate threshold and the rate of yawning exceeds a predetermined yawning rate threshold, for a predetermined number of frames.

In another aspect of this embodiment, the computing device detects any one of the drowsy state, and the eye gaze is to the left or to the right of the screen, while either the happy or neutral emotional states are detected and provides an indication of an inattentive state of the person. Additionally, the computing device detects either the sad or angry emotional states, and provides an indication of an emergency state of the person.

In an application of the present aspect and its embodiments, the person is a patient and the computing device is configured to control the display device to display preset digital therapy content and to control the audio output device to output accompanying audio with the digital therapy content. Here the at least one feedback includes controlling the display device to change the presented digital therapy content and controlling the audio output device to generate an alert in response to the inattentive state of the patient. Further in this application, when no drowsy state is determined and the eye gaze is directed to the display device, while either the happy or neutral emotional states are detected, the computing device pauses the digital therapy content on the display device, and resumes the digital therapy content on the display device. The at least one feedback can further include the computing device generating and transmitting an alert to a mobile device of a caregiver of the patient in response to the emergency state of the patient.

According to other embodiments of the first aspect, the computing device is configured to determine a left eye alignment as a first ratio of a number of left side white pixels to a number of right side white pixels of the left eye of the person, a right eye alignment as a second ratio of a number of left side white pixels to a number of right side white pixels of the right eye of the person, eye alignment stability as the absolute value of the ratio of the left eye alignment to the right eye alignment, and a classification of the eye alignment stability greater than a predetermined threshold and providing an output indicating the person exhibits strabismus.

In an alternate embodiment, the computing device is configured to determine strabismus from a video frame as input to a convolution neural network trained with eye regions segmented from 175 each strabismus and non-strabismus eye images, with at least specifications of an epoch of 600, batch size of 32, and image size of 100×100.

In another application of the first aspect and its embodiments, the person is a student participating in an online teaching lesson, and at least one feedback includes the computing device generating and transmitting an alert to a mobile device or computing device of a teacher leading the lesson in response to at least the inattentive state or emergency state of the student.

According to another embodiment of the first aspect, the screen is a windshield of a vehicle and the person is a driver of the vehicle. In this embodiment, the computing device is configured to detect from the captured video frames the at least one visual cue of rate of eye blinking and rate of yawning, and to measure and quantify their corresponding parameters. Here the computing device is configured to determine a drowsy state of the driver when the rate of eye blinking exceeds a predetermined blinking rate threshold and the rate of yawning exceeds a predetermined yawning rate threshold, for a predetermined number of frames. The computing device is further configured to determine proper head stability of the driver when a ratio of a number of frames with the driver's head oriented straight towards the windshield to the total number of frames captured over a predetermined period of time exceeds a predetermined head stability threshold. The at least one feedback includes controlling the audio output device to generate an alert in response to any one of the detected drowsy state of the driver and when the head stability of the driver falls below the predetermined head stability threshold.

In a second aspect, the present disclosure provides a method for real-time monitoring of attention level of a person. The method includes capturing video frames of a head and face of the person, where the head and face of the person are directed to a target area in front of them; processing each of the captured video frames to extract at least one visual cue of the person's head and face; analyzing the at least one visual cue to measure and quantify at least one parameter for comparison to corresponding predetermined ranges, where the corresponding predetermined ranges represent a correct level of attention by the person;

detecting the quantified at least one parameter falling outside of the corresponding predetermined range, and generating at least one feedback indicating the person is disengaged from the target area when the at least one quantified parameter is detected to fall outside of the corresponding predetermined range.

According to embodiments of the second aspect, the target area includes an electronic display device presenting preset graphics, images or videos for viewing by the person. The at least one visual cue measured and quantified includes eye gaze direction, rate of eye blinking and rate of yawning. The at least one visual cue measured and quantified includes an emotional state of the person as being one of happy, neutral, sad or angry. Analyzing can include determining a drowsy state of the person when the rate of eye blinking exceeds a predetermined blinking rate threshold and the rate of yawning exceeds a predetermined yawning rate threshold, for a predetermined number of frames. Detecting can include determining the drowsy state, and the eye gaze is to the left or to the right of the target area, while either the happy or neutral emotional states are detected and providing an indication of an inattentive state of the person. Detecting can further include detecting either the sad or angry emotional states, and providing an indication of an emergency state of the person.

In an application of the second aspect and its embodiments, the person is a patient and method further includes presenting preset digital therapy content on a display device as the target area, and outputting accompanying audio with the digital therapy content. Here, generating the at least one feedback includes changing the presented digital therapy content on the display device and outputting an audio alert in response to the inattentive state of the patient. Changing the presented digital therapy content can include pausing the digital therapy content on the display device, and resuming the digital therapy content on the display device when no drowsy state is determined, and the eye gaze is centered, while either the happy or neutral emotional states are detected. Generating the at least one feedback can further include generating and transmitting an alert to a mobile device of a caregiver of the patient in response to the emergency state of the patient.

In another application of the second aspect and its embodiments, the person is a student participating in an online teaching lesson, and generating the at least one feedback includes generating and transmitting an alert to a mobile device or computing device of a teacher leading the lesson in response to at least the inattentive state or emergency state of the student.

In yet other embodiments of the second aspect, the target area is a windshield of a vehicle and the person is a driver of the vehicle. Here the at least one visual cue measured and quantified includes rate of eye blinking and rate of yawning. Determining can include determining a drowsy state of the driver when the rate of eye blinking exceeds a predetermined blinking rate threshold and the rate of yawning exceeds a predetermined yawning rate threshold, for a predetermined number of frames. Determining can further include determining proper head stability of the driver when a ratio of a number of frames with the driver's head oriented straight towards the windshield to the total number of frames captured over a predetermined period of time exceeds a predetermined head stability threshold. Generating the at least one feedback includes generating an audio alert in response to any one of the detected drowsy state of the driver and when the head stability of the driver falls below the predetermined head stability threshold.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 8 shows example video frames of face images with eye gaze direction being detected, according to a present embodiment;

DETAILED DESCRIPTION

Figure 1:
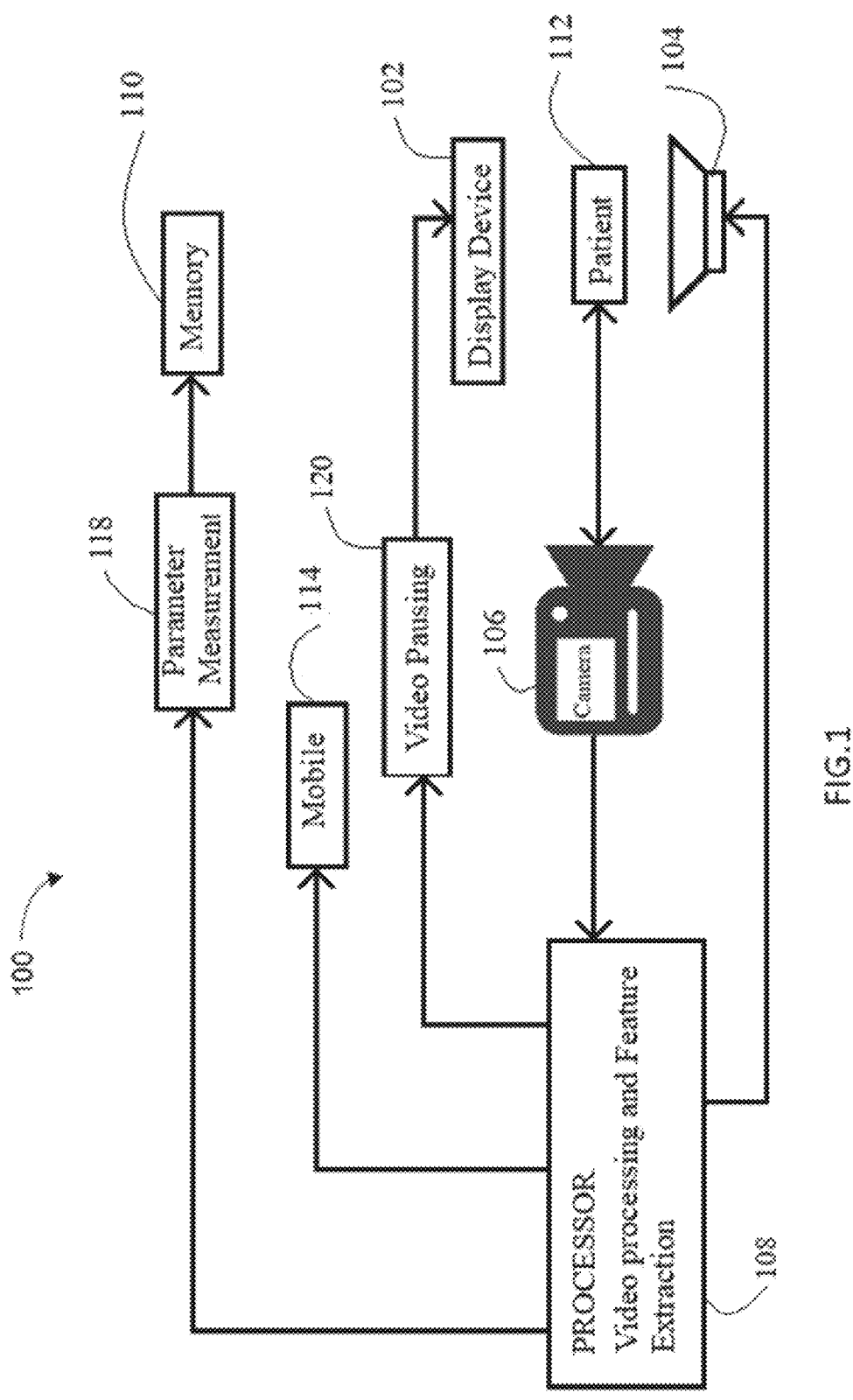
FIG. 1 is a block diagram of a digital therapy optimization system, according to a present embodiment.

Unless defined otherwise, all technical and scientific terms used herein have the same meaning as commonly understood by one of ordinary skill in the art to which this invention belongs.

As used herein, the term "about" refers to an approximately +/−10% variation from a given value. It is to be understood that such a variation is always included in any given value provided herein, whether or not it is specifically referred to.

The term "plurality" as used herein means more than one, for example, two or more, three or more, four or more, and the like.

The use of the word "a" or "an" when used herein in conjunction with the term "comprising" may mean "one", but it is also consistent with the meaning of "one or more", "at least one", and "one or more than one".

As used herein, the terms "comprising", "having", "including", and "containing", and grammatical variations thereof, are inclusive or open-ended and do not exclude additional, unrecited elements and/or method steps. The term "consisting essentially of" when used herein in connection with an apparatus, system, composition, use or method, denotes that additional elements and/or method steps may be present, but that these additions do not materially affect the manner in which the recited apparatus, system composition, method or use functions. The term "consisting of" when used herein in connection with an apparatus, system, composition, use or method, excludes the presence of additional elements and/or method steps. An apparatus, system composition, use or method described herein as comprising certain elements and/or steps may also, in certain embodiments consist essentially of those elements and/or steps, and in other embodiments consist of those elements and/or steps, whether or not these embodiments are specifically referred to.

Generally, the present disclosure provides a method and system for monitoring and optimizing human-device interactions. More specifically, the present disclosure provides embodiments of a method and system for real-time monitoring of a user, with optional real-time automatic user feedback to improve user adherence to a program or operation based upon detected physical attributes of the user. A program can be some executable software on a device that presents information for the user on a screen, such as a videogame or interactive graphics by example. An operation includes activities being executed by the user, such as driving a car by example.

All the presented embodiments of the method and system for monitoring and optimizing human-device interactions follows a state-based approach and in some embodiments uses feedback to regain the attention of the user.

In the presently described embodiments, the system employs computer vision technology to monitor and optimize human-device interaction by 1) utilizing computer vision technology to gather multiple sources of information pertinent to engagement and attention directly from the user, 2) combining and processing this information in real time to inform a state-based decision making algorithm, and in some applications, 3), providing feedback to optimize the human device interaction using example actions such as pausing the information being presented on the device, flashing messages on the screen, changing the content to regain engagement and/or providing an audio voice alert message asking the patient to "look at the video". The feedback can also include text or email messages sent to mobile devices of the caregiver, clinicians and/or parent of the patient. Those skilled in the art understand that such features can be programmed into a system.

The main objective of the real-time adherence monitoring system is to analyze and assess the attention state/level of a patient with respect to digitally presented material. One area of use, among other areas, is to assist the patient in maintaining proper engagement towards the digitally presented material. This is accomplished by extracting multiple attention cues that can be used to characterize engagement and compute automated material presentation schemes/regimes to assist the patient to achieve proper engagement. Applications of this invention are diverse, including, operational human-machine interaction, tele-control of machines, tele-operations of machines, operation of vehicles, and in treating visual as well as visual related disorders.

Different applications of the invention described herein are presented as embodiments. In one embodiment, there is provided a solution for the real time adherence monitoring and optimization via feedback of a digital therapy such as the use of specially programmed dichoptic videogames for amblyopia treatment. In such an embodiment the real time system is configured to monitor and optimize the videogame digital therapy for amblyopia and may detect that the patient is unhappy and is regularly looking away from the display device. Feedback to optimize the treatment could then involve changing the videogame being played, altering the difficulty of the game and/or alerting the caregiver/clinician. Additional types of feedback include haptic feedback, where such devices include such mechanisms, and audio feedback to the user whose attention to the operation or the program is required.

Other embodiments described herein provide real time monitoring of attention, emotional state and engagement for students in online teaching and real time driver fatigue detection and feedback, and provides a solution for the detection and monitoring of strabismus.

The embodiments of the system for use in digital therapies is now described as many of the concepts and algorithms are used in alternate embodiments directed to online teaching and real time driver fatigue detection and feedback.

According to a present embodiment, the system for monitoring and optimizing human-device interactions improves adherence to therapies that improve certain conditions related to vision disorders of an individual. Such conditions include amblyopia and strabismus by example.

The real time system of the present embodiment addresses the issue of patient adherence by monitoring treatment engagement and modifying treatment delivery or alerting the caregiver or health care professional if adherence fails. Previous attempts have monitored play time during videogame treatment using device-based metrics, but this has been found to be inadequate. What is needed is the monitoring of attentional engagement of the user which entails the monitoring of multiple parameters such as eye gaze, head position and emotional state which is achieved by the present embodiment. Furthermore, in addition to passive monitoring, present embodiment provides active feedback signal which could reengage the child by changing the video content in real time or by providing a feedback index of engagement. This feedback can take any form provided it attracts the attention of the patient to reengage with the video content, which has been programmed for a specific therapy.

The present embodiment can be used in the professional healthcare setting, such as a lab, hospital, clinic or other specialized location that the patient must visit. Although the patient is more likely to comply and engage more fully with the digital therapy at a specialized location, they may not be monitored and still can be distracted. Therefore, the present embodiment is effective for improving human-device interaction in all settings as it includes mechanisms for monitoring the patient and automatically providing the necessary feedback. Such monitoring will allow therapies to be conducted in a laboratory, clinic or hospital without a member of staff being dedicated to overseeing patients, thereby reducing costs. In addition, travelling to the specialized location may be inconvenient to the patient, and the specialized location may be inconvenienced as they must host the patient and use up a room which could otherwise be used for patients who truly need to be visiting.

Accordingly, home-based digital therapies are becoming increasingly popular for a range of neurological, psychiatric and sensory disorders, particularly for their convenience and also within the context of COVID-19. Executing the digital therapy at home and at any time to suit the schedule of the patient is a great convenience, and by itself improves the likelihood that the digital therapy is engaged. However, the success of digital therapies is critically dependent on patient adherence and engagement with the treatment, and this becomes an issue when the patient is in their private home setting with many potential distractions.

The presently described embodiment addresses the issue of patient adherence by monitoring treatment engagement and modifying treatment delivery or alerting the caregiver or health care professional if adherence falls. The embodiment enables the treatment to be "smart" by responding to changes in engagement to prolong treatment adherence. The primary application of the present embodiment is the treatment of vision disorders in children, and includes specific monitoring components for factors such as eye alignment. However variations of the present embodiment can be used generally for any home-based digital therapy for patients of any age. Accordingly, the present embodiment of the system for monitoring and optimizing human-device interactions is well suited for applications involving clinical trials where assessment of dose response is crucial and commercialization of digital treatments that utilize a telemedicine platform.

FIG. 1 is a block diagram of a digital therapy optimization system, being an embodiment of the system for monitoring and optimizing human-device interactions. The digital therapy optimization system 100 includes a display device such as a digital display screen 102, an audio output device such as a speaker 104, an image capture device such as a camera 106, and a computing system. The computing system includes at least one processor 108, a memory 110, wireless communication functionality (not shown), and a power supply (not shown). The at least one processor 108 can include a central processing unit and a chipset with the usual components to control any of the previously mentioned components, and to provide other typical computer processing functions. The computing system can be embodied as a mobile device, tablet or laptop computer with all the above mentioned components integrated therein, or as separate components like a desktop computer with the above-mentioned devices coupled to the processor 108 as peripherals. A mobile device 114 is shown as part of the alert system for providing some audio/visual alerts or notifications to a parent, instructor, or other authorized person of the status of the therapy initiated by the patient. The mobile device 114 is in communication with the processor 108 via well-known circuit elements configured for connecting to the Internet using wired or wireless configurations.

The camera 106 of the digital therapy optimization system 100 captures video of the patient 112. The memory 110 of the computing system stores programs executed by the at least one processor 108 to extract and compute relevant features from the captured video. The memory 110 can store the digital therapy content or material for display on display device 102, and can include accompanying audio for output on audio output device 104. Alternatively, the digital therapy content including video and audio can be streamed from the Internet. The processor 108 is programmed to measure parameters, as illustrated by functional block 118, of the patient 112 as determined using the camera 106 with the latter discussed algorithms. The memory 110 also stores measured parameters associated with the patient 112. These measured or estimated parameters are visual cues or features of the face and head of the person, as is discussed later in greater detail.

The measured parameters are processed in real time, and compared against preset thresholds. When they are exceeded, real-time feedback showing text prompts are provided to the patient to help him/her to maintain attention and engagement. Depending on the type of measured parameter threshold that is exceeded, different message prompts can be presented. For example, "remember to look at the screen" can be presented if the person is not looking directly at the screen, or "take a break" if a drowsy state of the person is detected. Another example of prompts on the display can be a colored dot system where a green flashing dot indicates attention compliance, while a red flashing dot indicates inattention, or a negative emotional state has been detected. This feedback can include at least one of an audio alert via the audio output device 104 and changing the information provided on display device 102. The audio alert and the visual information change should be sufficiently different from the content of the intended therapy in order to regain the attention and engagement of the patient.

The computed features mentioned above are metrics of identified physical features of the patient face. These computed features are extracted from the captured video from camera 106 and used to determine eye gaze, eye alignment, eye blinking, eye movement, eye orientation, and to assess attention and emotional state of the patient. Furthermore, the computed features are used to determine face orientation, yawning and to monitor and alter the behavior of the patient during the performance of intended tasks. Different parameters such as head stability (rate of change of head position), eye stability (rate of change of eye position with respect to time), reading related eye movements, relative position of one eye to the other (eye alignment stability), eye blink rate and rate of engagement can be measured with the present embodiment of system 100. The system 100 can work in open loop and closed loop mode. Open loop mode is used for measuring the level of attention and closed loop mode is used for both measurement and to provide feedback for behavioral compensation control strategies.

The digital display device 102 is used to present the digital material to the child or patient. A new development in binocular amblyopia therapy is the home-based dichoptic presentation of media content such as movies and cartoons. This approach is attractive because it can be used with young children who have superior amblyopia treatment outcomes to older patients but who cannot engage with video games. A Nintendo 3DS XL or another device that can present separate images to the two eyes (dichoptic presentation) without the use of colored lenses or other headwear is used for presenting digital material to a child or patient in some variations of the present embodiment. It is well known that the Nintendo 3DS system can display stereoscopic 3D effects without the use of 3D glasses or additional accessories. Alternately, the video can be presented using devices with auto-stereoscopic screens, lenticular screens which can be used for amblyopia treatment without the patient needing to wear special glasses. The patient is engaged in the treatment by viewing the dichoptic digital material. The camera 106 installed at the top of the screen of the display device is used to record video of the patient 112 in real-time. The video captured by the camera 106 in real-time is sent to the at least one processor 108 to extract and process the features from each frame and to initiate feedback commands if necessary.

This at least one processor 108 can be a CPU-GPU heterogeneous architecture where the CPU boots up the firmware and the CUDA-capable GPU comes with the potential to accelerate complex machine-learning tasks. Upon launching of the application or program configured for digital therapy optimization of the present embodiment, the validation of the appropriate patient commences by activating the camera 106 to capture video frames of patient. Once the video frame reaches the at least one processor 108, it performs face detection and facial recognition. It is assumed that the application has been initialized during a setup phase to capture and save reference video frames of the face of the appropriate patient. If the face does not match with the face of the intended patient, it sends an alert to the mobile device 114 of an instructor and/or parent indicating someone other than the intended patient is interfacing with the system. For example, siblings may accidentally engage with the digital media.

If the face is recognized, it extracts visual cues such as eye gaze, eye alignment, eye blinking rate, yawning, face orientation, emotion, and distance from the camera, and executes necessary computations to determine if the child is distracted or not paying attention to the presented content on the display device 102. If the child is not fully attending to the digital material that forms the treatment/testing, the system produces a feedback signal. The feedback may be in the form of words or phrases presented on the display device 102 such as "remember to watch the movie" or the system may pause or alter the digital media to regain attention. This video feedback control is shown in FIG. 1 with the functional block 120, which is an algorithm configured to execute the video feedback mechanisms discussed above for presentation on the display device 102. The loudspeaker 104 is used to produce any feedback sounds such as the above noted words or phrases.

The at least one processor 108 can be configured as a wi-fi hotspot and the display device 102 may be connected to the internet through this hotspot in order to access the animation video from Amazon AWS or some other similar streaming source. When the attention of the child is altered or when siblings watch the digital media, the media can be paused by disconnecting the wi-fi to the display device or the media can be modified in real-time in a way to redirect the user's attention. There are at least two situations when an alert is given to the parent/clinician via their registered mobile devices 114. 1) when siblings watch the video instead of the patient and, 2) when the patient feels sad or angry. In both situations, the system sends a message using IoT. The alert can be given using boto which is an Amazon Web Service (AWS) SDK of python. The alert is sent to the mobile device 102 of the parent and/or clinician.

Extracted cues from the video footage of the patient are used for the measurement of head stability (rate of change of head position), eye stability (rate of change of eye position), reading-related eye movements, the relative position of one eye to the other (eye alignment stability), eye blink rate, total eye stability, attentive engagement, and general engagement. Some of the extracted cues can be used to determine the emotional state of the patient, such as if they are happy, sad, angry or neutral. This information is extracted from the video footage in real-time using trained neural networks and spatial image processing techniques which are programmed into the software of the system and executed by the at least one processor 108. Measured parameters are also stored in memory 110 for later analysis of treatment adherence and to provide detailed analytics to assist in future treatment planning.

Figure 2:
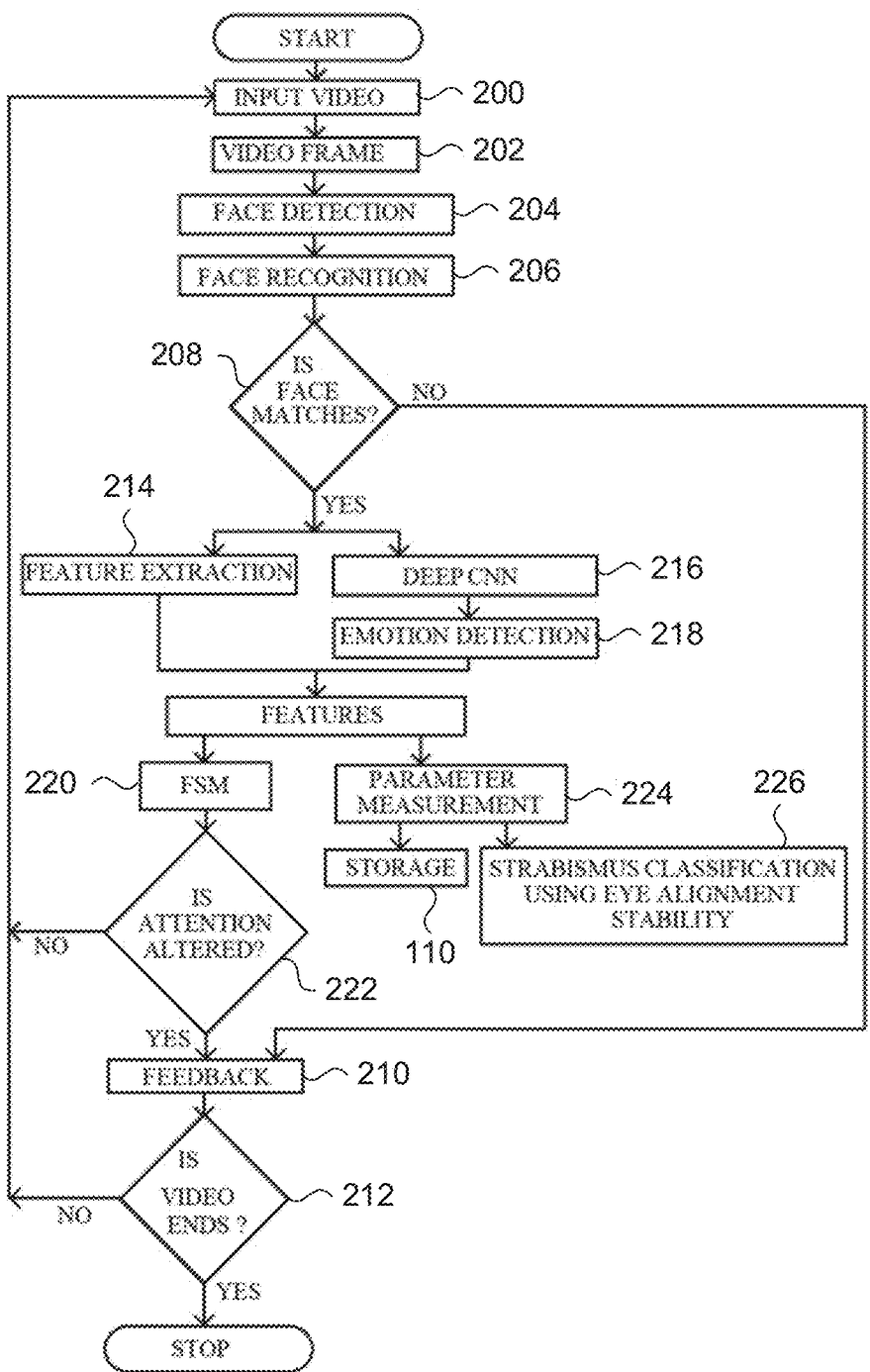
FIG. 2 is a flow chart of a method of digital therapy optimization using a system of FIG. 1, according to a present embodiment.

FIG. 2 is a flow chart of all processing steps performed for the implementation of the system depicted in FIG. 1, according to a present embodiment. It is assumed that the treatment application has been started and the treatment video (also known as digital therapy content) begins playing on the display device 102. Starting at step 200, input video (a video frame) is captured by the camera 106 that may be placed at the top of the screen of the display device 102. The captured video frame 202 is transferred to a face detection stage 204. The face is detected by the known haar cascade face detection algorithm. After the algorithm determines that a face has been detected in the video frame 202, face recognition proceeds at step 206 and is performed by the trained deep neural network based on Deep Residual Learning for Image Recognition, a known algorithm in the field of face recognition. This deep neural network extracts features from the face. These features are 128 face embeddings in the form of an array of numbers from both unknown and known faces and estimates the Euclidean distance between them. In an alternate embodiment, other known image processing techniques can be used to validate the proper person using the system, such as those used in mobile devices to unlock them. It is noted that steps 200, 202, 204 and 206 can be executed as part of set up of the application for the intended patient, with the facial data stored in memory 110 for later retrieval.

In the facial recognition step 206, these facial features are extracted from images of the faces of the user. These extracted features of the present video frame 202 are compared based on Euclidian distance with corresponding features of the facial data stored in memory 110 of the intended patient at step 208. In the present example, if the Euclidian distance is less than some tolerance, such as 0.6 for example, then a match is determined. If the face recognition fails, then some person other than the intended patient is engaged in the treatment and the system transitions to a feedback step 210. In this state, the system sends an alert to the parent or clinician with a suitable message indicating that someone other than the intended patient is engaged in the treatment. Following at step 212 a determination is made by the system to see if the video has ended, and if not, it can be paused before the method returns to step 200 to receive the next video frame. The above-described series of steps will continue to follow this loop until the face of the targeted patient is recognized at step 208. Returning to step 212, if it turns out the video has ended then the treatment is deemed complete for the present session and the method ends.

Figure 3:
FIG. 3 shows example consecutive video frame images of a patient deemed recognized by the system of FIG. 1, according to a present embodiment.

Returning to step 208, if face recognition is successful, meaning there is a close enough match of the data of the face in the video frame 202 to the face of the intended patient stored in memory 110, the system continues with the method. FIG. 3 shows an example of recognized faces after segmentation from each frame of the recorded video. While each image of the face is slightly different, all are determined to be recognized as the intended patient by the system.

Upon successful face recognition, the method proceeds to detect physical characteristics of the patient as part of a facial feature information extraction phase. At step 214, physical characteristics including face orientation, eye gaze direction, rate of eye blinking and yawning are detected. Further details of these physical characteristics and how they are determined are discussed later. Occurring in parallel is an execution of a trained deep Convolution Neural Network (CNN) at step 216 for detecting one of a limited set of emotions in the at least one video frame 2022 at step 218. Some of the above features are used in combination with the determined emotional state of the patient in a configured finite state machine (FSM) 220. The current state of the FSM is assessed at step 222 to determine that the attention of the patient has changed or not. If not, the method returns to step 200 to receive the subsequent video frame. Otherwise, the method proceeds to step 210 where some form of feedback is generated. As previously mentioned, this can include audio or visual feedback for the patient, and optionally an alert issued to the mobile device 114 of a parent or other authority. Details of the FSM 220 are discussed later.

Occurring in the same iteration of the method for each video frame 202, parameters based on the physical characteristics are measured at step 224, which include head stability, eye stability, reading-related eye movements, eye-alignment stability, eye blinking rate and engagement rate, and measurement of distance from the camera to the patient. These parameters are stored for later analysis of the progress of the treatment in memory 110. One specific condition to detect is strabismus at step 226, using eye alignment stability. Details of these measured parameters and strabismus classification of step 226 are discussed later.

The described method of the embodiment of FIG. 2 is executed iteratively for every video frame 202 for the duration of the digital therapy session, or until the session is prematurely ended. Details of how the specific features, emotions, and measured parameters are obtained is now described.

Face Orientation Analysis

Different approaches have been proposed by researchers in the field to estimate the head pose out of which some methods are model-based, and others are appearance or feature based methods. The main objective of face tracking is to analyze whether the child/patient is looking into the digital material presented for the treatment/testing. Face tracking is performed by estimating the pose of the head and the recognized faces are given as input to the face tracking system. Pose estimation starts with finding 2D coordinates of points from the face by using facial landmark detection which is an implementation of the face alignment method proposed in the paper by Kazemi, V.; Sullivan, J. "One millisecond face alignment with an ensemble of regression trees". In Proceedings of the IEEE Conference on Computer Vision and Pattern Recognition, Columbus, OH, USA, 23-28 Jun. 2014; pp. 1867-1874. The next step, after finding the facial landmark points, is the estimation of Euler's angle which in turn gives the head pose of the child/patient. Euler's angles are Pitch, Yaw, and Roll and represent the rotation of the head in 3D around X, Y, and Z-axis respectively. The Euler's angles are obtained from the extrinsic parameters [R][t] which are the translation and rotation matrix. These parameters are used to describe the camera moving around a static scene or the rigid motion of an object in front of a still camera.

The rotation matrix gives the Euler's angles. The points from the cheek, the tip of the nose, eyes, eyebrow, mouth, and chin are used as points in the face 2D coordinate system. Then these points are transferred to a 3D coordinate system normally referred to as the world coordinates system. Corresponding points in the camera co-ordinate system can be obtained with the help of translation and rotation parameters. The 'solvePnP function on OpenCV python implements a Direct Linear Transform (DLT) solution followed by Levenberg-Marquardt optimization to find rotation and translation parameters. This function takes the input as an array of object points in the world coordinate space, an array of corresponding image points in the 2D image plane, an input camera matrix, and distortion coefficients obtained by camera calibration. The rotation vector is converted into a matrix and is concatenated with a translation vector.

Euler's angle is obtained by cv2.decomposeProjectionMatrix API that produces six properties. After finding Euler's angles (Pitch, Yaw and Roll), a threshold is set for these parameters to determine whether the face is oriented towards the camera or not. The values of these angles to one side are taken as positive and to the opposite side are taken as negative. The face is said to be oriented straight, when the range of variation of these parameters in degrees are below fixed thresholds, for example $-5<=$pitch$<=10$, and $-20<=$yaw$<=20$, $-20<=$roll$<=20$.

Figure 4:
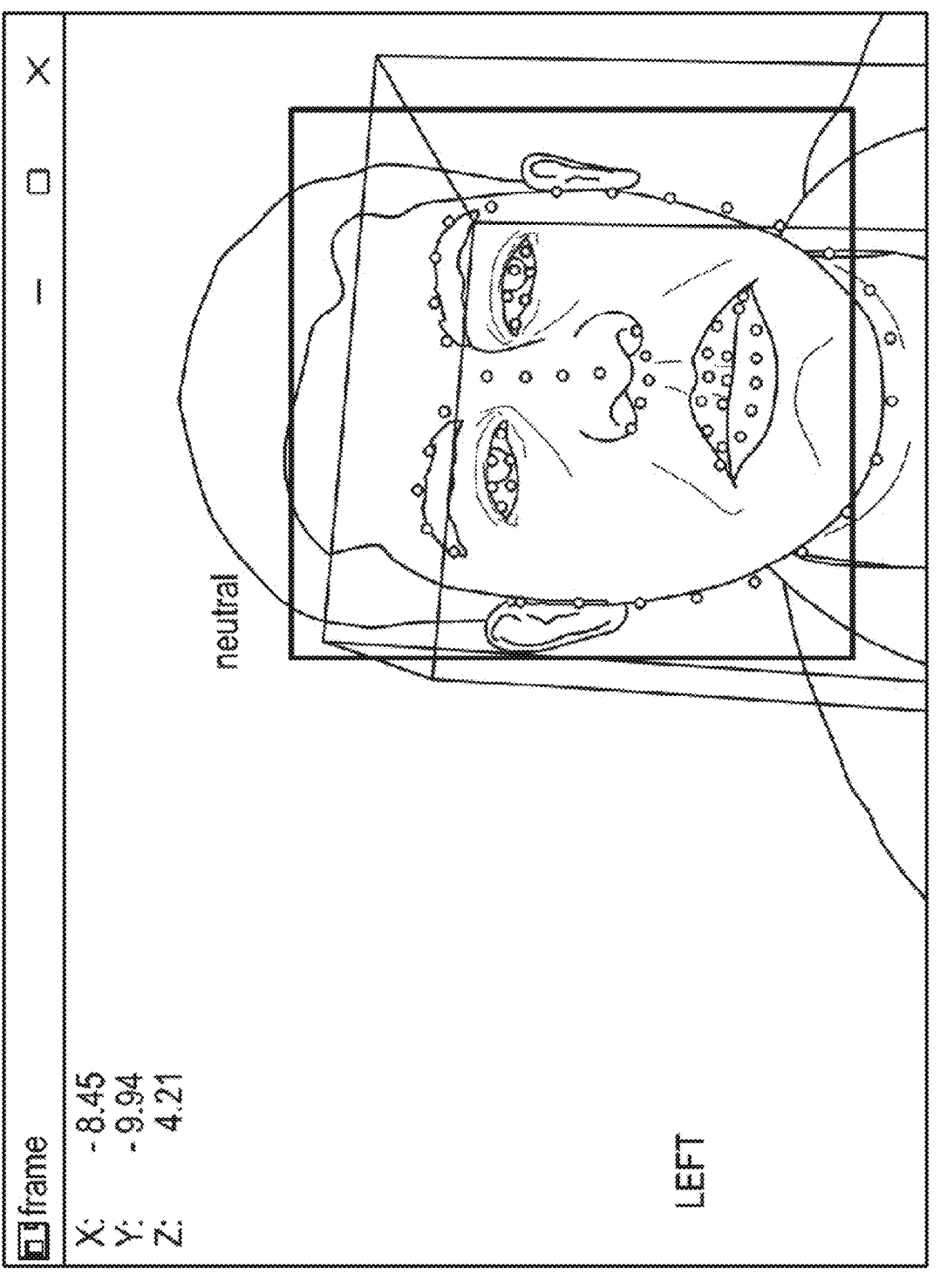
FIG. 4 shows an example head pose calculated by the system of FIG. 1 as not being straight, according to a present embodiment.
Figure 5:
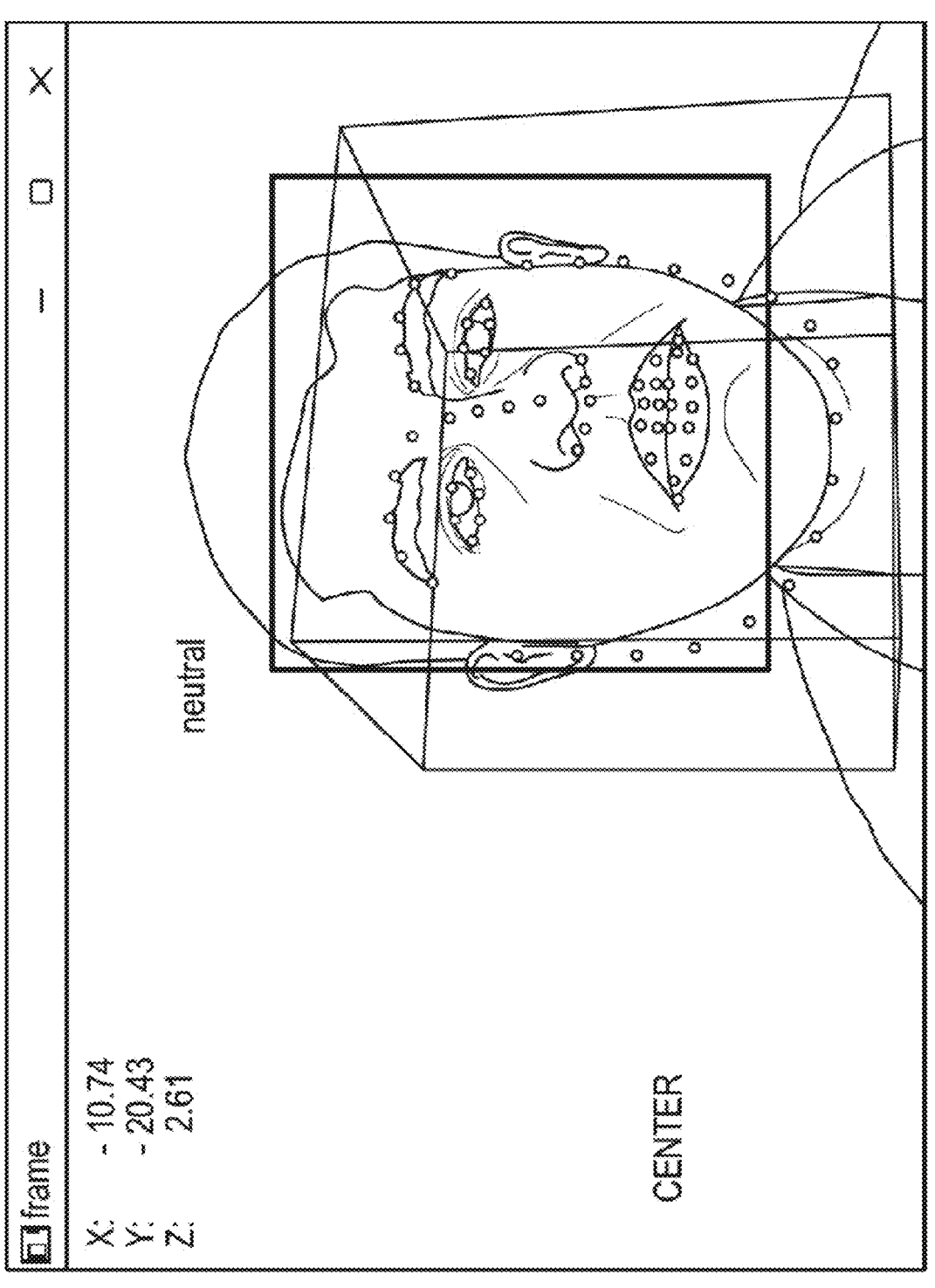
FIG. 5 shows another example head pose calculated by the system of FIG. 1 as not being straight, according to a present embodiment.
Figure 6:
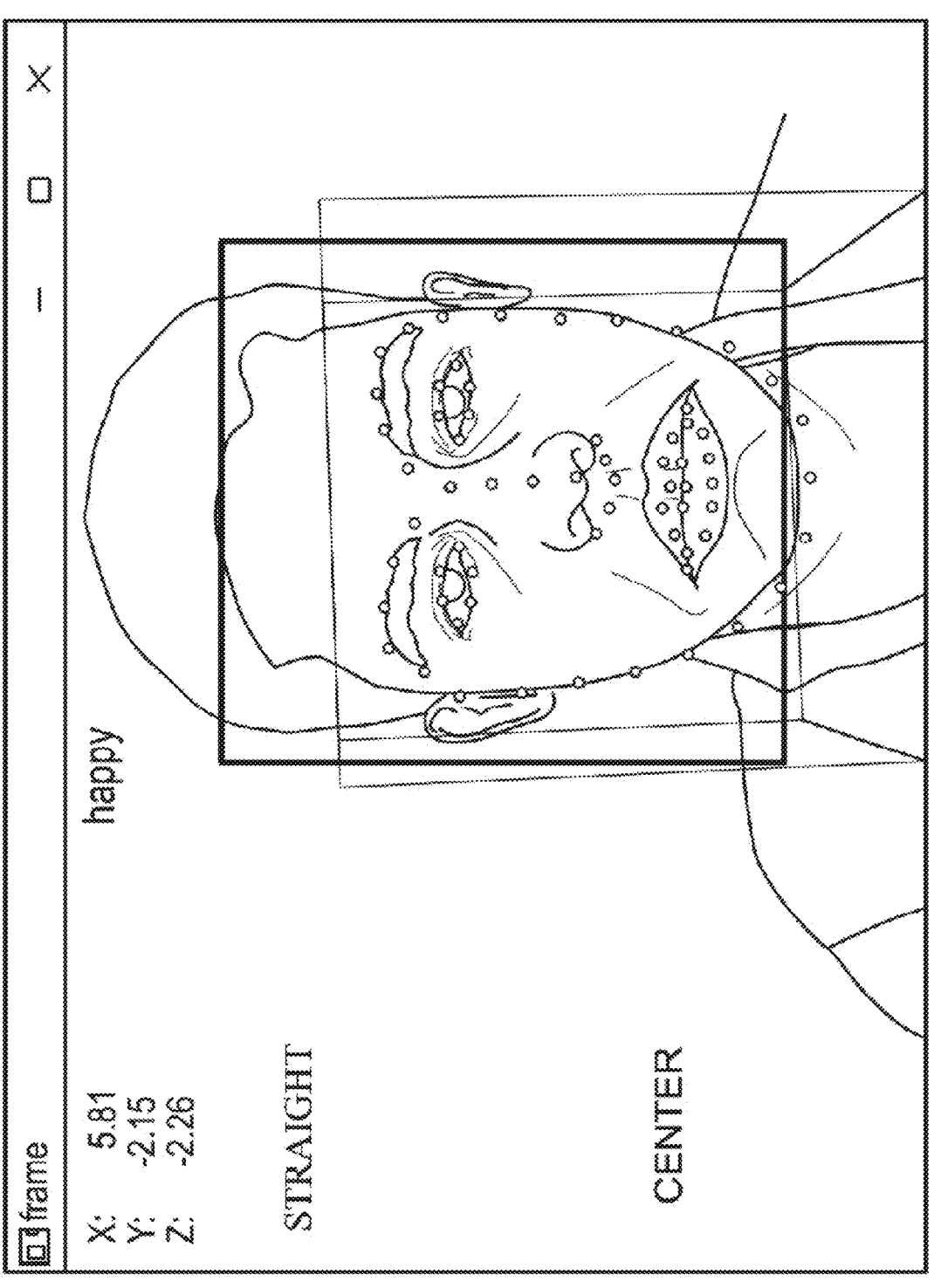
FIG. 6 shows an example head pose calculated by the system of FIG. 1 as being straight, according to a present embodiment.

Example poses are shown in FIGS. 4 to 6, where X denotes pitch, Y denotes yaw and Z denotes roll. In FIG. 4, the pose is automatically determined by the system as not straight since the value of pitch is outside the range defined for the straight position. Similarly, for FIG. 5 also, the pose is automatically determined by the system as not straight. In FIG. 6, the values of all angles are in the specified range and hence the pose is designated as straight.

According to an alternate embodiment, when the system is used with younger children, the roll angle is not considered. This is due to the fact that young children have a tendency to orient their heads such that the value of the roll is high but are still looking at the content of the display. For example, the child could be resting his/her cheek on a table while having eyes directed at the display device and still maintaining attention to the displayed content.

For the sake of simplicity, 'EA' using the product fusion rule as given in equation (1) below, when the threshold for pitch and yaw is set to 25.

$$EA = \text{Pitch} * \text{Yaw} \tag{1}$$

This variable is used to find the head pose or face orientation by setting a threshold which is empirically found to be 625. Different face orientation methods known in the art can be used in the system of the present embodiment, with roll values being ignored.

Eye Gaze Estimation

Figure 7:
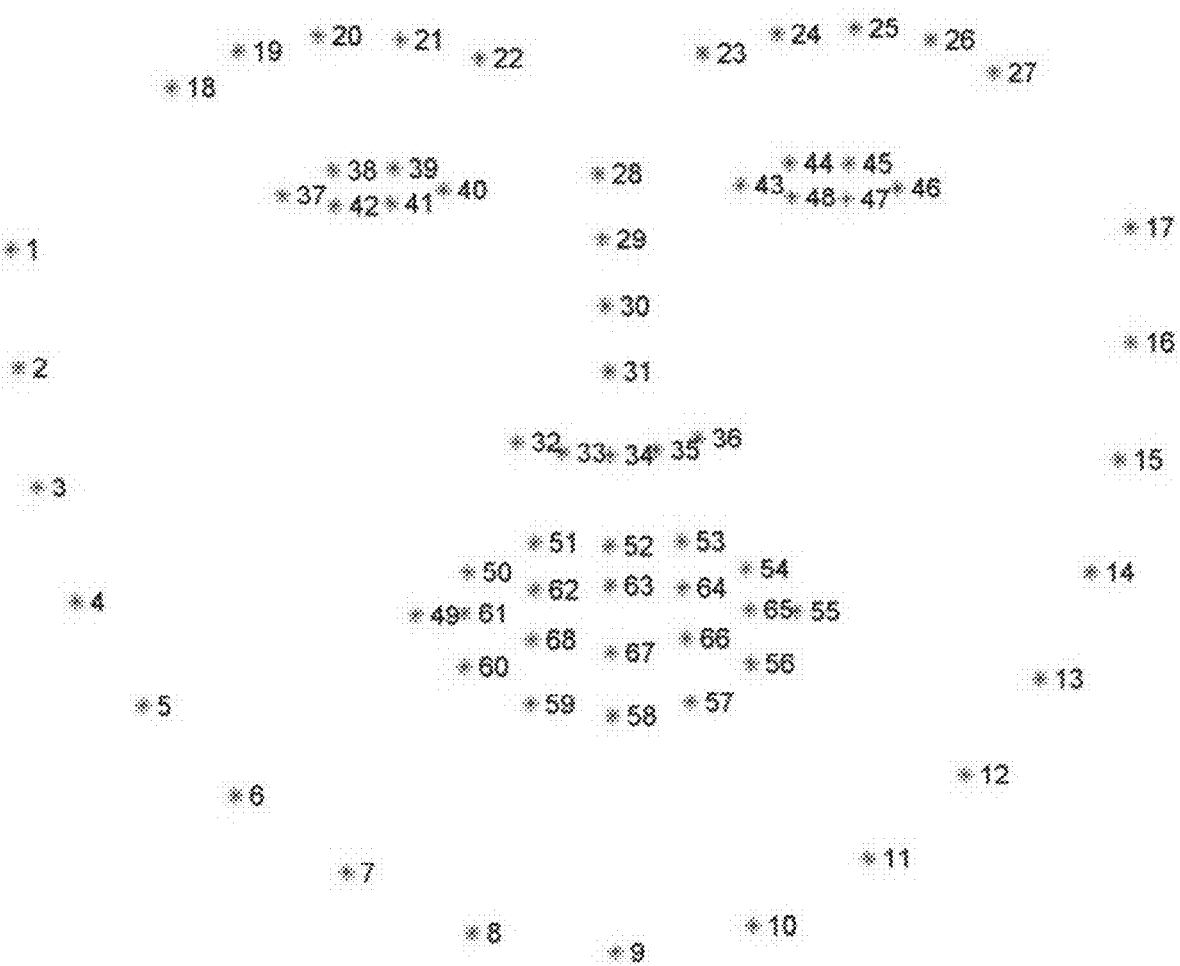
FIG. 7 is a mapping of facial landmarks with 68 preset coordinate points.

Different eye gaze tracking systems are proposed in the literature, some of which are appearance-based methods, such as the one proposed in the paper by Anuradha Kar, Peter Corcoran "A Review and Analysis of Eye-Gaze Estimation Systems, Algorithms and Performance Evaluation Methods in Consumer Platforms" DOI 10.1109/ACCESS.2017.2735633. Researchers have used facial points along with support vector machines (SVM) for finding the position of the iris, as proposed in the paper by Y.-L. Wu, C.-T. Yeh, W.-C. Hung, and C.-Y. Tang, "Gaze direction estimation using support vector machine with active appearance model," Multimed. Tools Appl., pp. 1-26, 2012. The recognized face images have been the input to the iris tracking stage as regions of interest. Eye gaze is extracted from this region of interest to track the iris of the patient. Eye region is segmented from the selected region of interest using a 68 facial landmark detector available in Dliblibrary. Dlib is a Python programming library used for computer vision, machine learning and data analysis applications. FIG. 7 shows an example illustration of these points arranged on an area of a face. These landmarks give the coordinates of the 68 points in the face. Points from 37 to 42 and 43 to 48 gives the boundary of the left and right eye regions respectively.

After finding out the boundary, a mask is used to extract the eye portion from the face. This eye region is converted into a gray scale image and is in turn converted into a binary image by the application of a threshold. This binary image may consist of some noisy regions that are removed by the application of morphological operations known as opening and closing. The ratio of the number of white pixels at the two sides of the iris is found from the resulting image. Consider the case of left eye. Let us take 'lsw' as the number of pixels at the left side of the iris and 'rsw' is the number of white pixels at the right side of the iris. The gaze ratio of the left eye is then defined as:

$$\text{gaze\_ratio\_left\_eye} = lsw/rsw \tag{2}$$

Similarly, the gaze ratio of the right eye can also be found and is designated as "gaze_ratio_right_eye". Then the eye gaze 'Eye_gaze' is defined as $$Eye\_gaze = (gaze\_ratio\_right\_eye + gaze\_ratio\_left\_eye)/2 \quad (3)$$

A threshold is set for Eye_gaze to detect the exact position of the iris. The threshold for Eye_gaze is estimated empirically. For example, if the value of Eye gaze is less than 0.8, the iris is facing right. If the value is in between 0.8 and another threshold of 3, the iris is at the center; otherwise its position is considered to be facing left. The mentioned thresholds are examples which have been empirically determined. FIG. 8 shows example video frames of face images with eye gaze, where the position of the iris automatically detected by this method is also shown.

Eye Blinking Detection

Eye aspect ratio is used for eye blinking detection and is a feature used for drowsy state detection, as shown in the paper by Dhaval Pimplaskar, M. S. Nagmode, Atul Borkar, "Real Time Eye Blinking Detection and Tracking Using Opencv" Int. Journal of Engineering Research and Application www.ijera.com ISSN: 2248-9622, Vol. 3, Issue 5, September-October 2013, pp. 1780-1787. Reference is made to the landmark points of FIG. 7 which are utilized for eye blinking detection in the present embodiment. After the recognition of the face, facial land mark points are detected from the face region as previously described. Six facial land mark points (43, 44, 45, 46, 47, and 48) are annotated on an example image of a person's left eye shown in FIG. 9.

$(x_1, y_1)$ and $(x_2, y_2)$ represents the coordinates of the points 44 and 45 respectively. Then the coordinates of point C (annotated in FIG. 9) are given as $$x_C = \frac{(x_1 + x_2)}{2}, y_c = \frac{(y_1 + y_2)}{2} \quad (4)$$

Figure 9:
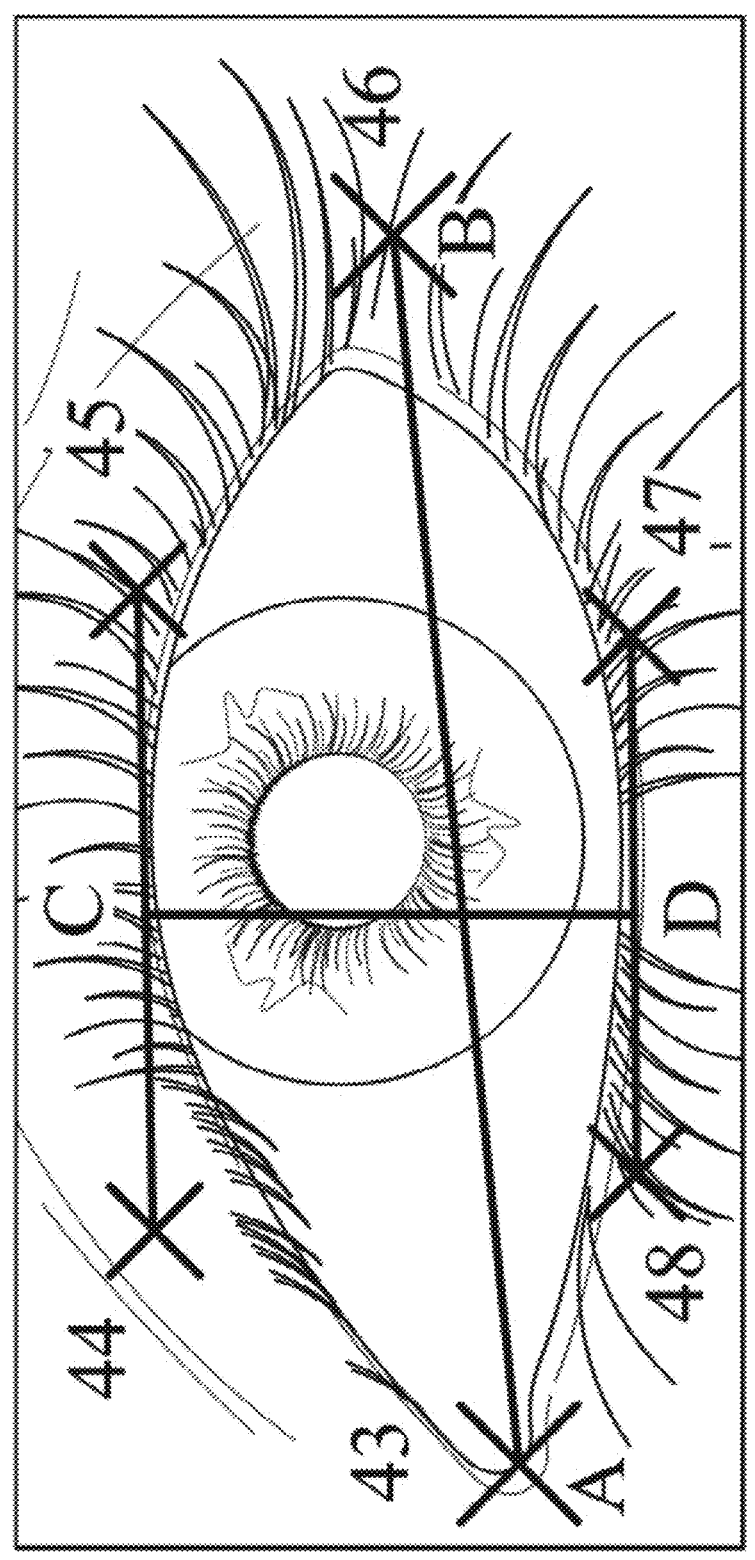
FIG. 9 is an illustration of a person's left side eye with annotations of six facial landmark points.

Similarly, the coordinates $(X_D, yD)$ of point D (annotated in FIG. 9 are also found. Then the length of the line CD is obtained by the distance formula.

$$\sqrt{(x_C - x_D)^2 + (y_C - y_D)^2} \quad (5)$$

Similarly the length of the line AB is also estimated, where point A coincides with point 43 and point B coincides with point 46 (A and B annotated in FIG. 9). Then the aspect ratio of the right eye is obtained as $$REAR = \frac{AB}{CD} \quad (6)$$

Similarly the aspect ratio of the left eye is also found and is designated as 'LEAR'. Then the eye blinking ratio is obtained as $$EBR = \frac{LEAR + REAR}{2} \quad (7)$$

Figure 10:
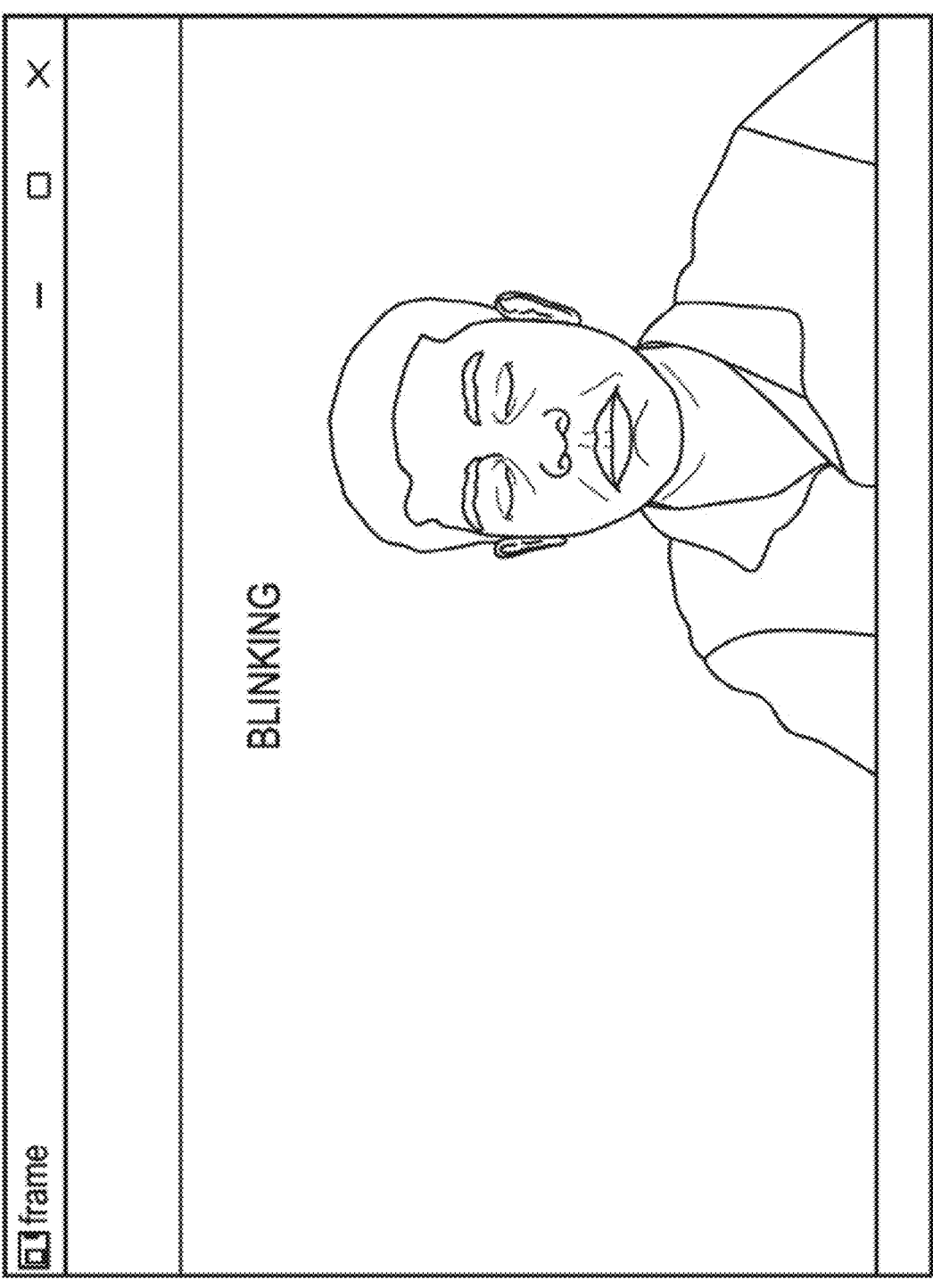
FIG. 10 shows an example of automatic blinking detection, according to a present embodiment.

FIG. 10 shows an example of eye blinking automatically detected by the above procedure from a video frame. In the context of the present embodiments, a brief eye closure is more indicative of drowsiness or fatigue, versus blinking. Hence the present embodiments detect blinking versus a brief eye closure over a predetermined duration of time that could be indicative of drowsiness or fatigue. The blinking was detected when the value of the eye blinking ratio is greater than a threshold of 5.4. This threshold has been empirically identified by plotting eye blinking ratios in real time under different lighting conditions. It is noted that frame rate of the video has a significant impact on the value of the threshold for the number of frames that the eyes are closed. The video recorded in real-time experiments was 10 fps. Hence a threshold of 40 frames indicates eye closure for 4 seconds, which is longer than a typical blinking movement. In fact, if the eye is closed continuously for more than 4 seconds, the patient/child is considered to be in a drowsy state. For a video with 30 fps, this threshold is set as 120 frames.

Yawning Detection

Figure 11:
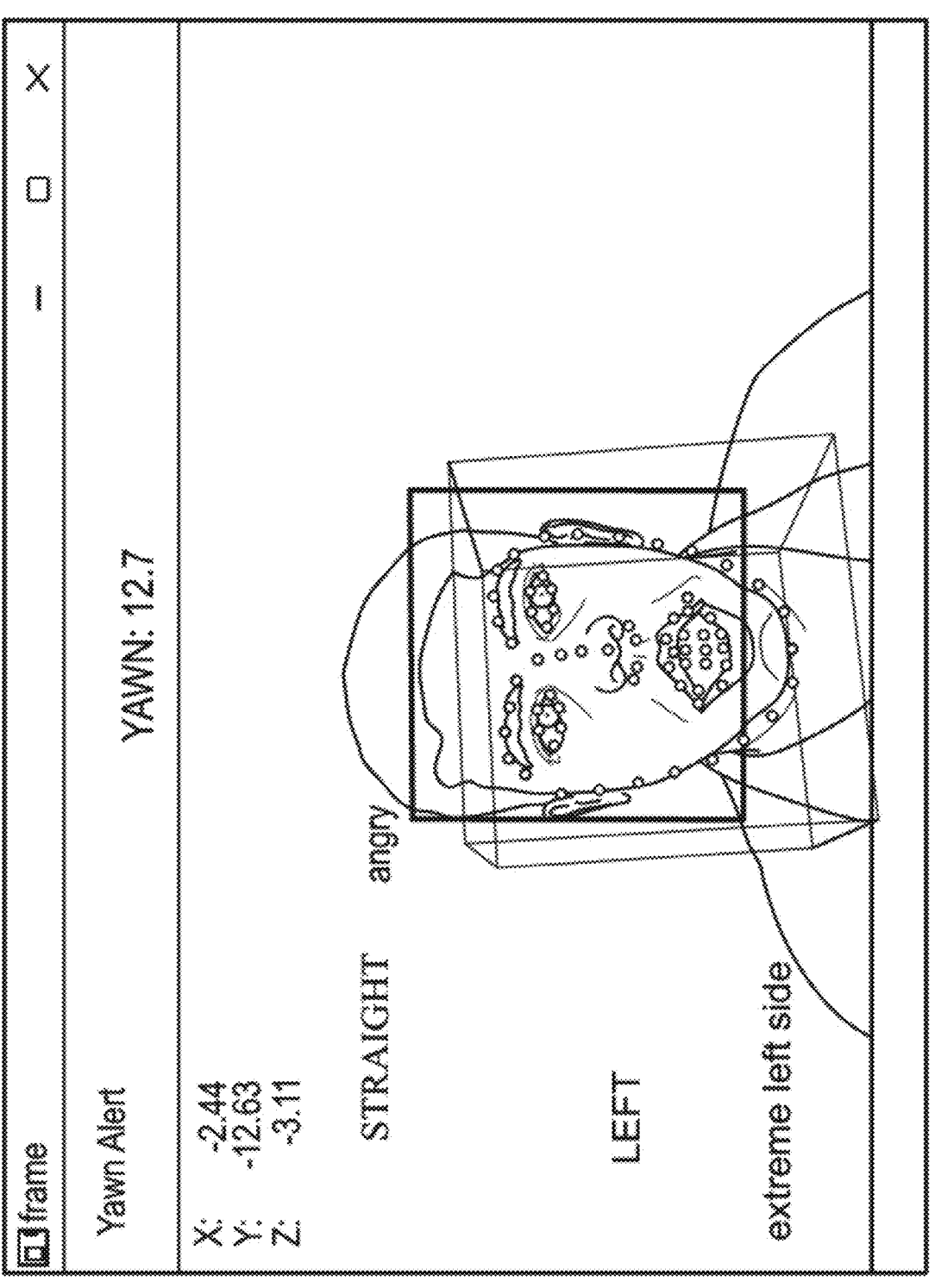
FIG. 11 shows an example of automatic yawning detection, according to a present embodiment.

The yawn is modeled as a sequence of large vertical mouth openings. When the mouth starts to open, the mouth contour area starts to increase. The mouth normally opens much wider in yawning conditions compared to speaking and the mouth opening cycle is longer in the yawning situation. This helps to differentiate yawning from speaking, smiling and other similar situations. Yawning detection supports an indication of drowsiness, and is performed as follows. The recognized face region is first converted to a gray scale image. Facial landmark points are detected from this face region by using a function in dlib library. The facial landmark points are (x, y) coordinates within the face and are referred to as a "shape". There are the 68 points as shown in FIG. 7. This shape form is then converted into a numpy array. The top lip is obtained by the points 50 to 53 and 61 to 64 as shown in FIG. 7. Similarly, the bottom lip is detected by the points from 56 to 59 and 65 to 68. After that the coordinates of the middle point of the top lip and the bottom lip are found by taking the mean of these points. The distance between these two middle points, Yawning Ratio (YR), is obtained by the distance formula. A threshold is set for this distance to detect the yawn situation, such that a yawn is detected when the threshold is exceeded over a predetermined number of frames. This threshold can be determined empirically by plotting the value of YR for every frame of videos for a number of individuals. The yawn automatically detected by this method is shown in the example of FIG. 11.

Details of a subroutine for detecting a drowsy state from video frames is as follows with reference to the flowchart of FIG. 12. This subroutine for detecting a drowsy state is executed in the feature extraction step 214 of FIG. 2. Example threshold values of T2=5.4 and T3=10 are set for eye blink rate (EBR) and yawn rate (YR) respectively. These threshold values can be determined by examining the graph plotted between these parameters against frame count, where actual values of T2 and T3 obtained from every frame are plotted against the corresponding frame number, and when yawning or eye blinking occurs, the corresponding values are noted. This process can be done for multiple individuals to obtain more data. During no yawning conditions, its value varies around 4. The value of the lip distance has a sharp increase when the yawning has been detected. According to the present embodiment, the method starts by initializing a frame counter (FC) to zero at step 300. The algorithm takes a first video frame as the input. Then face detection and face recognition are performed at step 302. The face recognition can use the same techniques described for step 206 of FIG. 2. Assuming the correct person's face is detected, the method resumes with EBR estimation at step 304 and YR estimation at step 306.

At steps 308 and 310 the estimated EBR and YR are compared to the preset thresholds of T2 and T3. If EBR>T2, then the frame counter is incremented at step 312 (FC=FC+ 1). If EBR<=T2, it checks for YR>T3 and if it is true, the algorithm proceeds to step 312. After incrementing FC at step 312, the algorithm checks for whether FC=T (which is the number of frames equal to 4 seconds in a present example) at step 314. If it is yes, the drowsy state is detected at 316 and the method restarts by returning to 302 after resetting FC to zero at step 317. If it is no, the next video frame is analyzed as the method loops back to step 302. The effect of the drowsy state, which is one of the extracted features of FIG. 2, is to trigger a feedback response to the patient, which is described in further detail later.

Returning to steps 308 and 310, when both YR and EBR are less than or equal to their respective thresholds, then the frame counter is reset to zero at step 318, takes the next frame and returns to 302.

Emotion Recognition

Deep learning network-based approaches have been used for emotion recognition of children and are limited in number. A deep Convolution Neural Network (CNN) proposed in the paper by Octavio Arriaga, Paul G. Ploger and Matias Valdenegro "Real-time Convolutional Neural Networks for Emotion and Gender Classification" arXiv: 1710.07557v1 [cs. CV] 20 Oct. 2017 has been used for emotion recognition from the face. This architecture is called mini-Xception implemented by the modification of the Xception model proposed by Francois Chollet "Xception: Deep learning with depthwise separable convolutions" CoRR, abs/1610.02357, 2016.

In the experimental implementation of the presently described system, the database for the training of CNN neural network was obtained from the Institute of Child Development, University of Minnesota, Minneapolis, United States. This database of children consists of images of 40 male and female models with seven emotions with faces oriented in different directions. Another database having seven emotions of FER2013 also has been used for the training. The regularization used is 12 and a data generator is also used to create more images. The epoch of 110 with a batch size of 32 is selected for the training of the neural network. The softmax activation is performed at the output layer of the network, and "relu" activation is used in the intermediate layers.

Maxpooling 2D layer down samples the input representation by taking the maximum value over the window defined by pool size for each dimension along the features axis. In fact, the model uses the same architecture as the mini-xception CNN network. The CNN was trained to identify facial expressions relating to the emotions Happy, Sad, Disgust, Neutral, Anger, Surprise and Scared. All the Images are pre-processed before feeding to the network. The size of the images is considered as (64, 64, 1) pixels. Different pre-processing steps performed on the images include normalizing, resizing, and expansion of the dimension of the channel. The labelling of each image is converted into a categorical matrix. The pre-processed database is split into training and testing sets. The training set is used to train the model and has been saved to use in the real-time system. The testing set has been used for the validation of the model.

Figure 13:
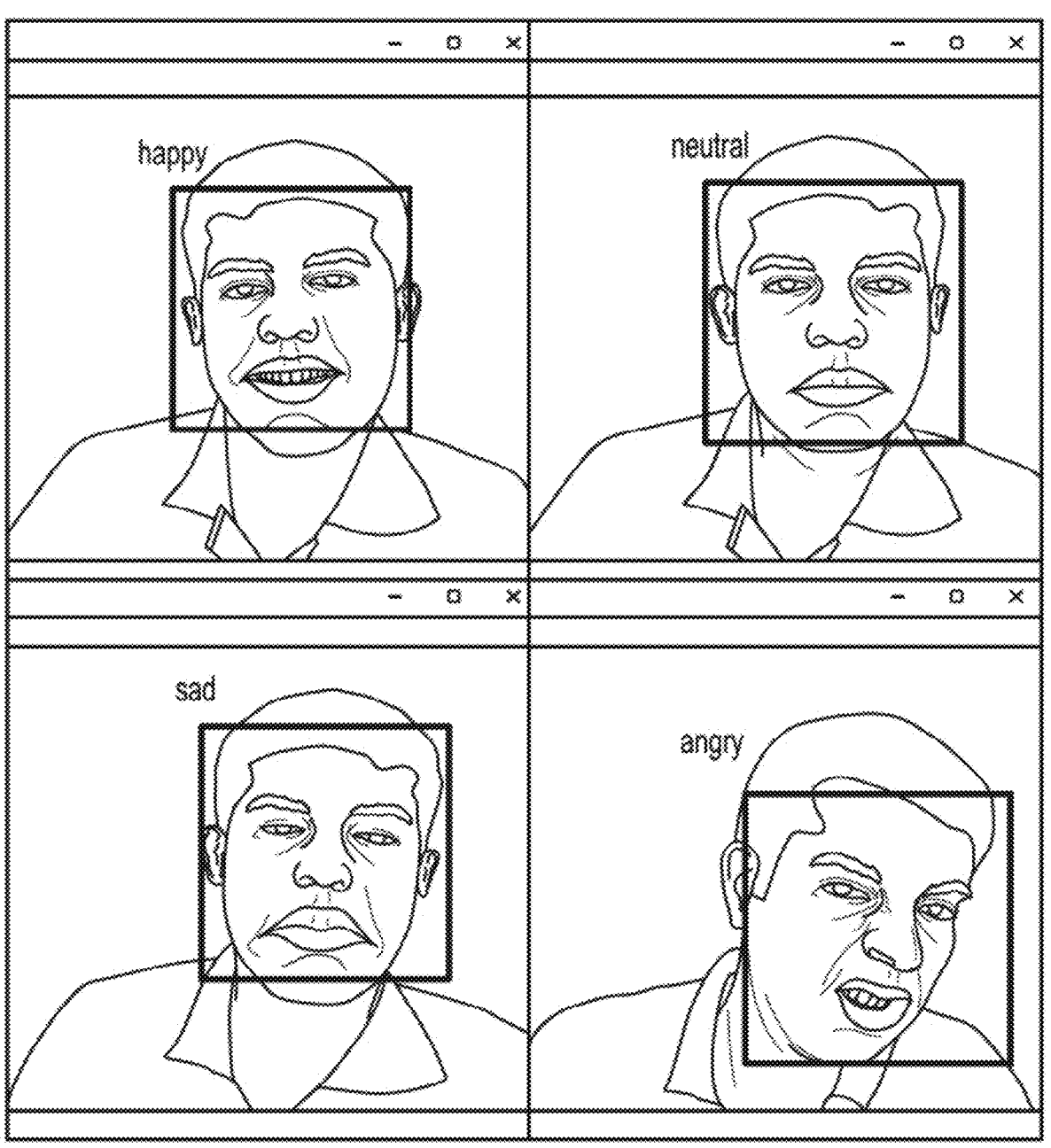
FIG. 13 shows example video frames of face images with automatically detected emotional states, according to a present embodiment.

In a real-time system, a face is detected from each frame of the video and is pre-processed reshaped and converted into gray scale. This face is fed into the trained model for emotion recognition. The trained model predicts the probability for each emotion and outputs the most probable emotion. FIG. 13 shows examples of automatically detected facial expressions, where each example image has been automatically annotated with the detected emotions of happy, neutral, sad and angry.

The proposed real-time digital therapy optimization embodiment of the proposed embodiment uses these four emotions, happy, neutral, sad, and angry. These four emotions can give information about the comfort level of the/patient during the treatment. This detected emotional state of the patient helps provide feedback to the parent or clinician.

With reference to FIG. 2, after the feature extraction, detected emotions and the presence of any drowsy state being detected are passed to the Finite State Machine (FSM) 220 for providing feedback. The feedback is provided by the FSM with three states and the changes of the states are determined by the conditions defined for the features.

Implementation of Feedback

Figure 14:
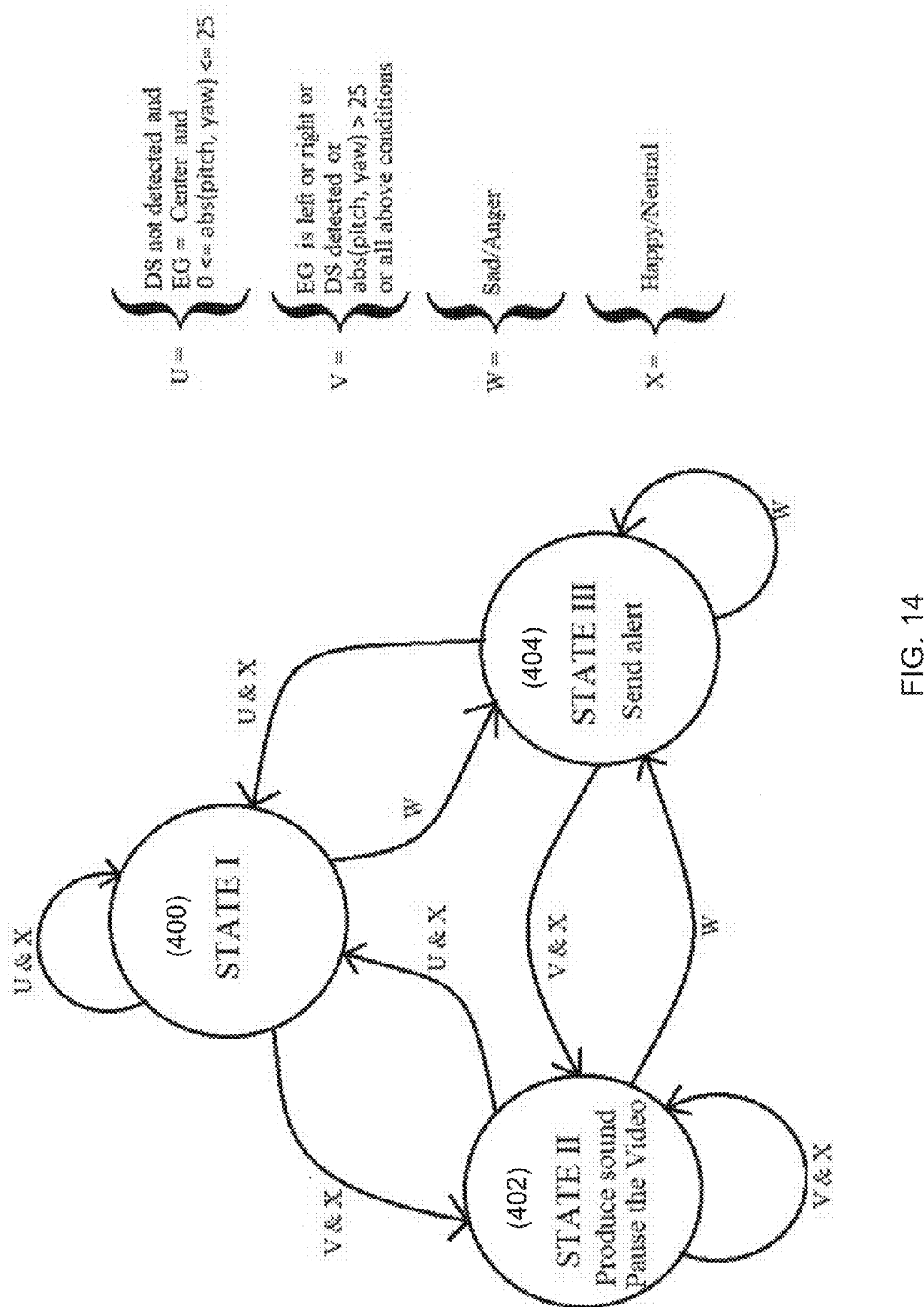
FIG. 14 is a diagram of a Finite State Machine for the implementation of the feedback, according to a present embodiment.

The implementation of feedback is needed in the digital therapy optimization embodiment of the system to try and ensure the constant participation of the patient in the treatment. The system can adopt a finite number of states depending upon the behaviour of the child during the treatment. A finite state machine (FSM) with three states has been implemented in the present embodiment to regain the attention of the child/patient towards the digital material presented on the display device 102. FIG. 14 shows the FSM diagram designed for the proposed system according to a present embodiment. The conditions for state transitions are written along the arrows and are defined on the right-hand side of the diagram. If the system does not undergo any state transitions, the arrows starts and ends at the same state. The states are STATE I (400), STATE II (402), and STATE III (404).

The transition of the system from one state to another is triggered by extracted visual cues. The system changes to or remains in STATE I when eye gaze is at the center, no drowsy state is detected, the face oriented straight-ahead and detected emotions are happy or neutral. The system changes to STATE II when any or a combination of the following events occurs for more than a pre-set duration of time, such as four seconds by example. With the system configured to have a frame rate of 10 frames per second (fps), the threshold is equal to 40 frames. At 30 fps, the threshold is equal to 120 frames. These events are (eye gaze (left or right) or (drowsy state is detected) or absolute value of pitch and yaw is in between 0 and 25 each. The system remains in the STATE II until the requirements for STATE I or STATE III are met. In STATE II, the system can provide a variety of different feedback types including prompts to the patient through the speaker, pausing of the digital media or changing the digital media to regain attention.

The system changes to STATE III, when emotions become sad or angry continuously for four seconds, or the equivalent number of frames for a given fps of the system. The system changes to STATE III from any other states depending upon the occurrence of sad or angry emotions, in fact the system gives the more priority to STATE III. Assume for example a situation where eye gaze is at the left side, the face oriented towards the camera, there is no drowsy state, and the detected emotion is angry. This situation satisfies the conditions for both STATE II and III. In this case, the system will go to state III since STATE III has the highest priority.

The conditions for the state transitions and corresponding feedback actions are further explained below. Consider T1, T2, and T3 are the thresholds for EA (Euler's Angle), EBR (Eye Blinking Rate) and YR (Yawning Ratio) respectively. These parameters have been previously discussed, along with their corresponding predetermined thresholds. Assume T4 and T5 are the lower and upper thresholds of EG (Eye gaze), also a previously described parameter with corresponding predetermined thresholds which has been discussed already. The system remains in STATE I, if EA<=T1 (or 0<=abs (pitch, yaw)<=25), DS (Drowsiness) is not detected (EBR<=T2 and YR<=T3), EG at center (T4<=EG<=T5) and EL=neutral/happy. In this state, the system does not provide any feedback. Transition from STATE I to STATE II, if DS is detected (EBR>T2 or YR>T3) or Eye gaze at the left side or right side (EG<T4 or EG>T5) or EA>T1 and EL=neutral/happy. Any or all of the conditions should be valid for 4 seconds for example. The system can be configured to produce words or phrases designed to reengage the patient such as "remember to watch the movie", pauses the digital content or changes the digital content. If DS is not detected (EBR<=T2 or YR<=T3) and Eye gaze is central (EG<=T4 or EG=>T5) and EA<=T1 and EL=neutral/happy the system reverts to STATE I.

The system remains in STATE II, as long as its condition is satisfied. Transition from STATE II to STATE III, if EL=Sad/Angry for more than 40 frames (four seconds) by example, the system sends alerts to the clinician or parents via their mobile device. The transition from STATE III to STATE II, if EL=Neutral/happy and DS is detected (EBR>T2 or YR>T3) or Eye gaze at the left side or right side (EG<T4 or EG>T5) or EA>T1. If any or all of the conditions should be valid for an example 40 frames (4 seconds based on a 10 fps configuration) then the system produces feedback actions as described above. The system remains in STATE III, If EL=Sad/Anger for more than an example of 40 frames. The system sends alerts to the clinician or parents. The transition from STATE III to STATE I, if EL=Neutral/ happy and EA<=T1, DS (Drowsiness) is not detected (EBR<=T2 and YR<=T3), T4<=EG<=T5. In this state, the system does not provide any feedback. The transition from STATE I to STATE III, if EL=Sad/Anger for more than an example 40 frames, the system sends an alert to the clinician or parents via their mobile device. The algorithm for this example FSM is given below,

```
Frame number N
FC_STATE_III = 0
FC_STATE_II = 0
Start
If emotion = (sad or angry) then
        i. FC_STATE_III = FC_STATE_III +1
        ii. If FC_STATE_III = 40 then
        a. Send message
        b. Reset FC_STATE_III = 0
Else if (EG = center and (DS not detected) and
(0 <= abs (pitch, yaw) <= 25) and
(emotion is neutral or happy)) then
        Change System to STATE I
Else ((EG =left/right) or (DS detected) or
(abs (pitch, yaw) > 25) and (emotion is
neutral or happy))
        FC_STATE_II = FC_STATE_II +1
        If FC_STATE_II = 40 then
    Change System to STATE II
        Generate voice or pause the video or change the
        Digital content
        Reset FC_STATE_II = 0
```

```
N= N+1
Go to start
Returning to FIG. 2, the step of measuring
parameters 224 is described in further
detail.
```

The computed visual cues are used to measure various parameters that are intended for the analysis of the progress of the patient/child who have undergone the digital therapy. These parameters are now defined and include head stability (rate of change of head position), eye stability (rate of change of eye position with respect to time), reading-related eye movements, relative position of one eye to the other (eye alignment stability), eye blink rate, total eye stability, attentive engagement and general engagement.

Head Stability (HS)

Estimation of the overall head stability during the treatment is performed by setting two counters, one is to count the number of frames with 0<=(absolute value of pitch and yaw)<=25 and the second counter is to find the total number of frames. Hence the head stability is obtained by the following equation.

$$HS = \text{(Number of frames with } 0 <= \text{(pitch, yaw)} <= 25)/ \quad (8)$$
$$\text{(Total number of frames)}$$

It can also be estimated by average of the ratio of the number of frames within which 0<=(absolute value of pitch and yaw)<=25 per minute to the total number of frames per minute.

Eye Stability (ES)

Eye stability is a measure of the ability to concentrate on the digital therapy or other task. Eye gaze ratio is a suitable measure of eye stability, the eye gaze is at left or right side means that eye stability is not good, and the patient or operator is looking away from the device. When the gaze is centered, eye stability is good. The measurement of overall eye stability is estimated by setting two counters, one is to count the number of frames with eye gaze is at the center, and another to count total number of frames. Then the eye stability is obtained with the help of equation (9) below.

$$ES = \text{(Number of frames with Eye Gaze at center)/} \quad (9)$$
$$\text{(Total number of frames)}$$

Total eye stability is estimated by the fusion of eye stability (ES) and eye blinking rate (EBR). In the present embodiments, the weighted sum fusion rule is used for the estimation of total eye stability. Thus total eye stability is obtained as $$TES = 0.9 * ES + 0.1 * EBR \quad (10)$$

Equal weight of 0.9 is given to eye stability and 0.1 is given to eye blinking rate Reading-Related Eye Movements Reading-related eye movements involve reading from left to right, from right to left and fixations at some point of a line of text then going back. The parameter which measures this reading related eye movement is eye readability. This is estimated by finding the ratio of the number of white pixels on the two sides of the iris. The region from the left corner of the eye to the right corner is divided into five regions according to the threshold set for eye readability. These are extreme left, quarter left, the middle region, quarter right, and extreme right. Reading starts from the extreme left and passes through quarter left, middle, quarter right, extreme right. According to the movement of the iris, these regions are shown on the screen. For example, if the reading stops in the middle of the line and goes back to the starting of the line, eye movement also stops in the middle and then shows the extreme left. If 'lsw' is the left side white pixels and 'rsw' is the right side white pixels of an eye region, and then the eye readability is obtained by $$LEA = lsw/rsw \qquad (11)$$

The value of eye readability varies from 0 to 2, if the iris is at the left side of the eye and its value is one when the iris is at the center and greater than one if the iris is at the right side of the eye.

Eye-Alignment Stability (EAS)

Eye alignment stability is an important parameter that gives information about strabismus (eye misalignment). Eye-alignment stability is estimated as follows $$LEA = LELSW/LERSW \qquad (12)$$

$$REA = RELSW/RERSW \qquad (13)$$

where LEA is left eye alignment which is the ratio of the number of left side white pixels and right side white pixels of the left eye, REA, is right eye alignment and is the ratio of the number of left side white pixels and right side white pixels of the right eye, LELSW=No. of left side white pixels of the left eye, LERSW=No. of right side white pixels of the left eye, RELSW=No. of the left side white pixels of the right eye, RERSW=No. of right side white pixels of the right eye. Then eye alignment is obtained as $$EAS = \text{Eye alignment stability} = \qquad (14)$$
$$\text{Abs}[(\text{Alignment\_left\_eye}) - (\text{Alignment\_right\_eye})]$$

Eye Blinking Rate and Engagement Rate

Eye blinking rate is defined as the ratio of number of frames with eye blinking to the total number of frames. It provides information about the attentive engagement of the patient/child in the test. The engagement rate is divided into general engagement and attentive engagement. The duration of general engagement (DGE) is decided by two factors, face orientation and eye gaze. It is defined as the ratio of number of frames with eye gaze at center and absolute value of pitch and yaw being between 0 and 25, to the total number of frames. Similarly, the attentive engagement is defined by the ratio of number of frames with State I to the total number of frames which include all the visual cues except emotion. This gives more precise information about the engagement of the child/patient in the test/treatment than duration of general engagement. The values of head stability, eye gaze stability, general engagement, total eye stability and attentive engagement vary from 0 to 1. These parameters can be classified into different ranges as poor, fair, good and excellent, according to its ranges 0 to 0.5, 0.5 to 0.7, 0.7 to 0.85 and 0.85 to 1 respectively. The eye blinking rate is classified into very low, low, high and very high depending upon its rages from 0 to 0.3, 0.3 to 0.5, 0.5 to 0.8 and 0.8 to 1 respectively.

Strabismus Eye Detection Using Eye Alignment Stability (EAS)

With reference to FIG. 2, the step of strabismus classification 226 can be optionally executed after finding the EAS. Strabismus is a state in which the eyes are not properly aligned with each other during fixation. It can cause amblyopia if it persists for long time and is known to be often unstable. The present embodiments can be used to detect strabismus in real time from images and video inputs. According to the current strabismus detection embodiment, after finding the EAS, its absolute value is used to differentiate a strabismic (deviated) eye from a non-strabismic (fixating) eye. If the absolute value of the eye alignment stability is greater than a particular threshold (T6), then the eyes are not aligned and if the is less than the threshold, the eyes are aligned.

Figure 15:
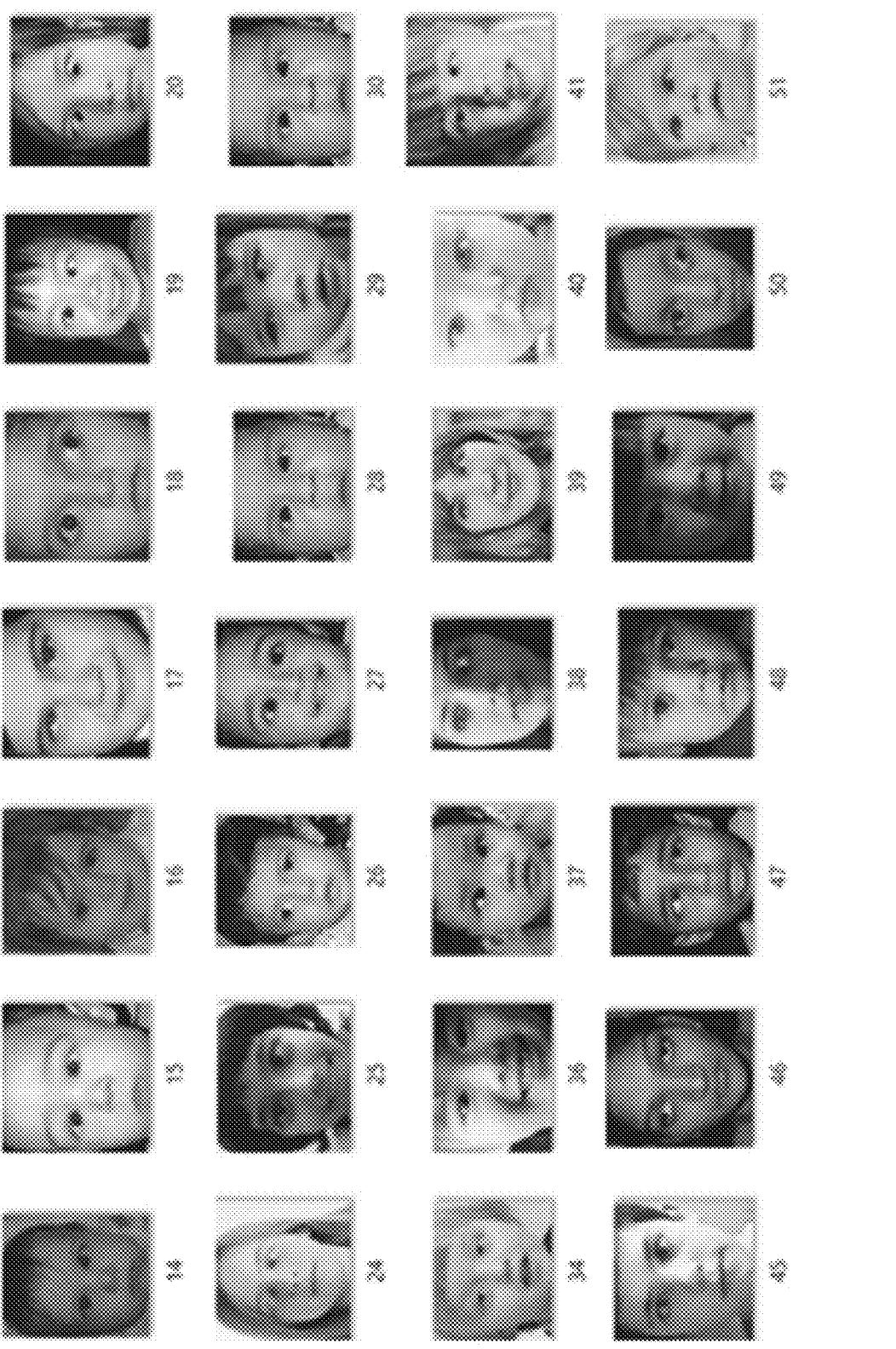
FIG. 15 shows the images used for examining eye alignment stability.
Figure 16:
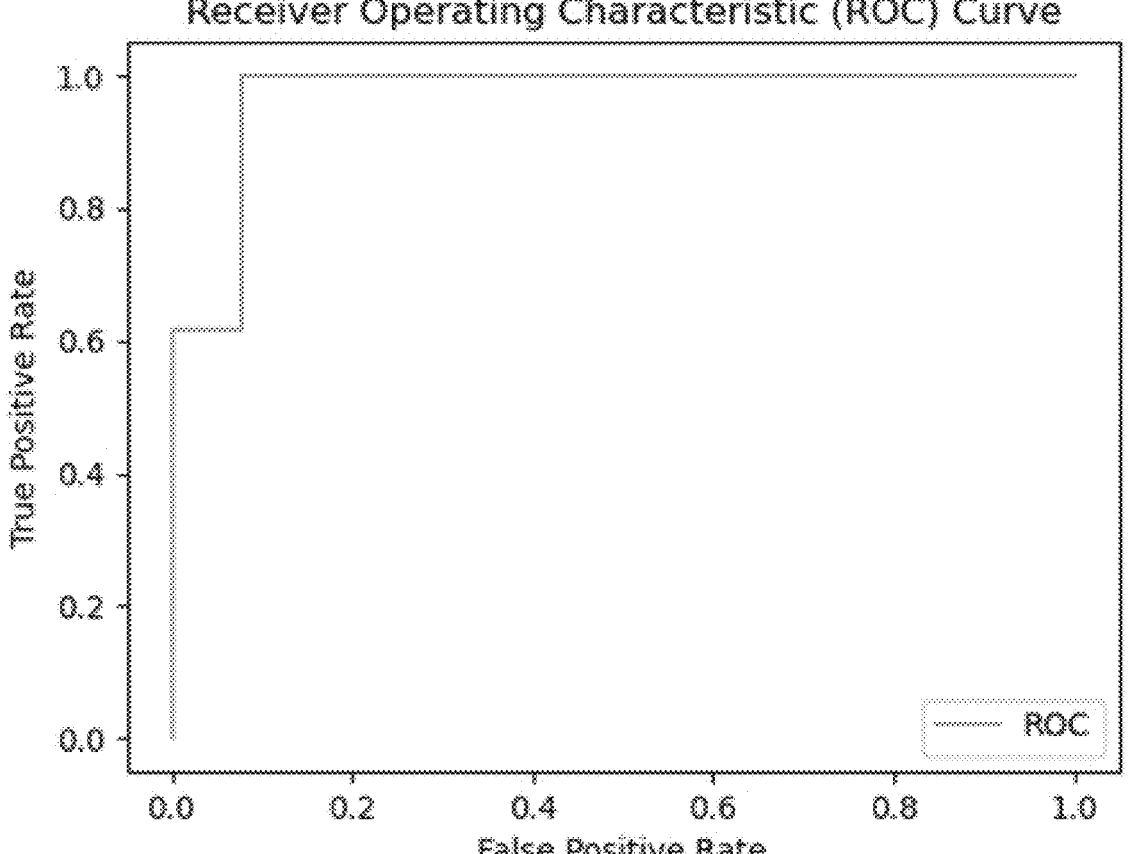
FIG. 16 is an ROC curve for the classification of strabismus (eye misalignment) and non-strabismus eyes using the eye alignment stability measure of the present embodiment.

Both eyes are well aligned if the value of EAS is zero. A database of publicly available images of children with and without strabismus was collected and analyzed, where examples of these publicly available images are shown in FIG. 15 and used for examining eye alignment stability. These images are collected from Google photos. For the present embodiment, a threshold of 0.2 is set to eye alignment stability for the classification of strabismus and non-strabismus images. This means that whenever EAS is greater than 0.2, the corresponding image is classified as non-strabismus and otherwise it is strabismus images. The ROC curve for this classification is shown in FIG. 16. The strabismus eye is taken as a positive class and the non-strabismus eye is taken as a negative class. The test produced a True Positive Rate (TPR) of 100% and a False Positive Rate (in percentage) of 7.69%.

Strabismus Eye Detection Using Convolution Neural Networks

Figure 17:
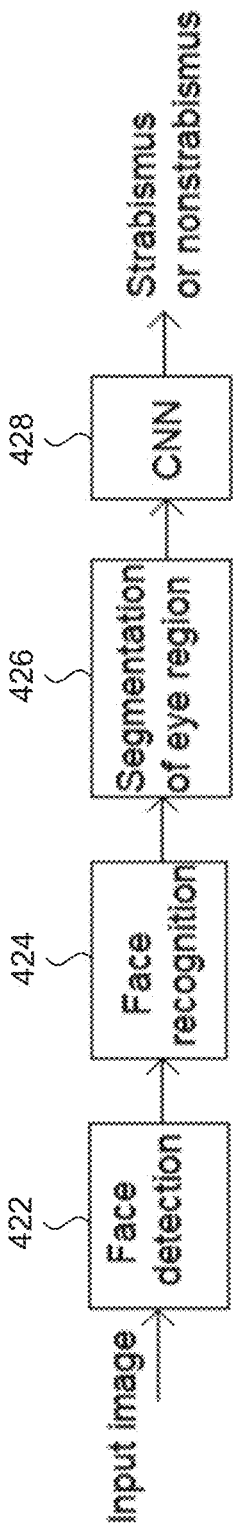
FIG. 17 is A flow diagram of a CNN based strabismus detection method, according to a present embodiment.

An alternate method for executing strabismus classification according to the present embodiments is to use a convolution neural network (CNN). A flow diagram of the CNN based strabismus detection method is shown in FIG. 17. The input image of a video frame is passed to the face detection stage 422 and it detects the faces present in the image. The face is detected by the known haar cascade face detection algorithm. After the face detection stage, a face recognition stage 424 performs face recognition of the person in the image by the trained deep neural network based on Deep Residual Learning for Image Recognition. This deep neural network extracts 128 face embeddings in the form of an array of numbers from both unknown and known faces and estimates the Euclidean distance between them. Face recognition is successful if this distance is less than a threshold value, such as 0.6 for example. The eye region is segmented from the recognized face image by using 68 facial land points at stage 426. In order to segment the eye region, facial landmarks points are detected from the recognized face image using a 68 facial landmark point detector. The eye region is segmented from the face using these lad mark points.

Figures 18A, 18B:
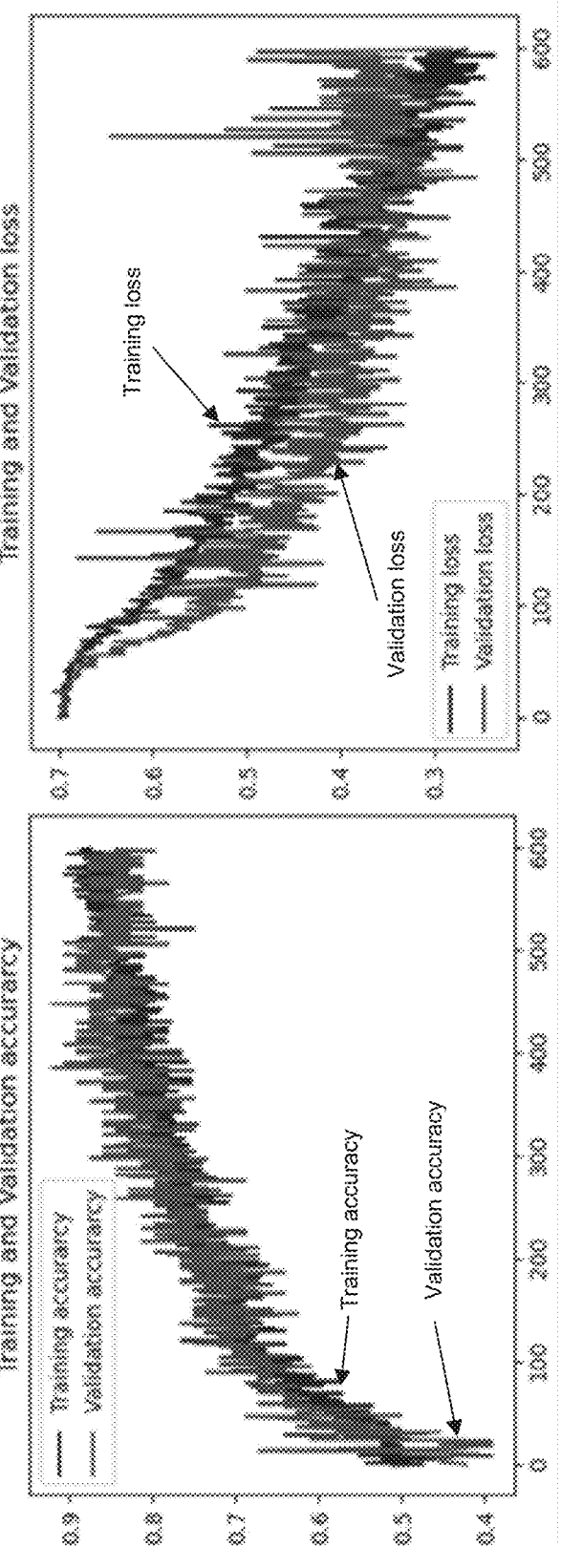
FIG. 18A is a graph showing training and validation accuracy for the CNN based strabismus detection method of the present embodiment.
FIG. 18B is a graph showing training and validation loss for the CNN based strabismus detection method of the present embodiment.

In order to detect the strabismic eye, a VGG-16 convolution neural network (CNN) with some changes to the architecture is used at stage 428 since it is the most widely used CNN for classification. This VGG-16 architecture consists of 5 convolution layers conv1, conv2, conv3, conv4, and conv5 with a filter size of 32, 64, 128, 128, and 512 respectively. The inner layers use the relu activation function and the output layer uses the sigmoid activation function since this layer has two classes. This CNN architecture also used a drop-out layer to reduce overfitting. The architecture is trained with eye regions segmented from 175 each strabismus and non strabismus eye images which are collected from Google images. The specifications used for the training are an epoch of 600, batch size of 32, and image size of 100×100. In order to validate the trained model, 21 images of strabismus and non strabismus eyes are used. The training accuracy and validation accuracy of the CNN training is shown in FIGS. 18A and 18B. Both increase as it approaches an epoch of 600. Similarly, training and validation loss are also reduced to zero with an epoch of 600.

Figure 19:
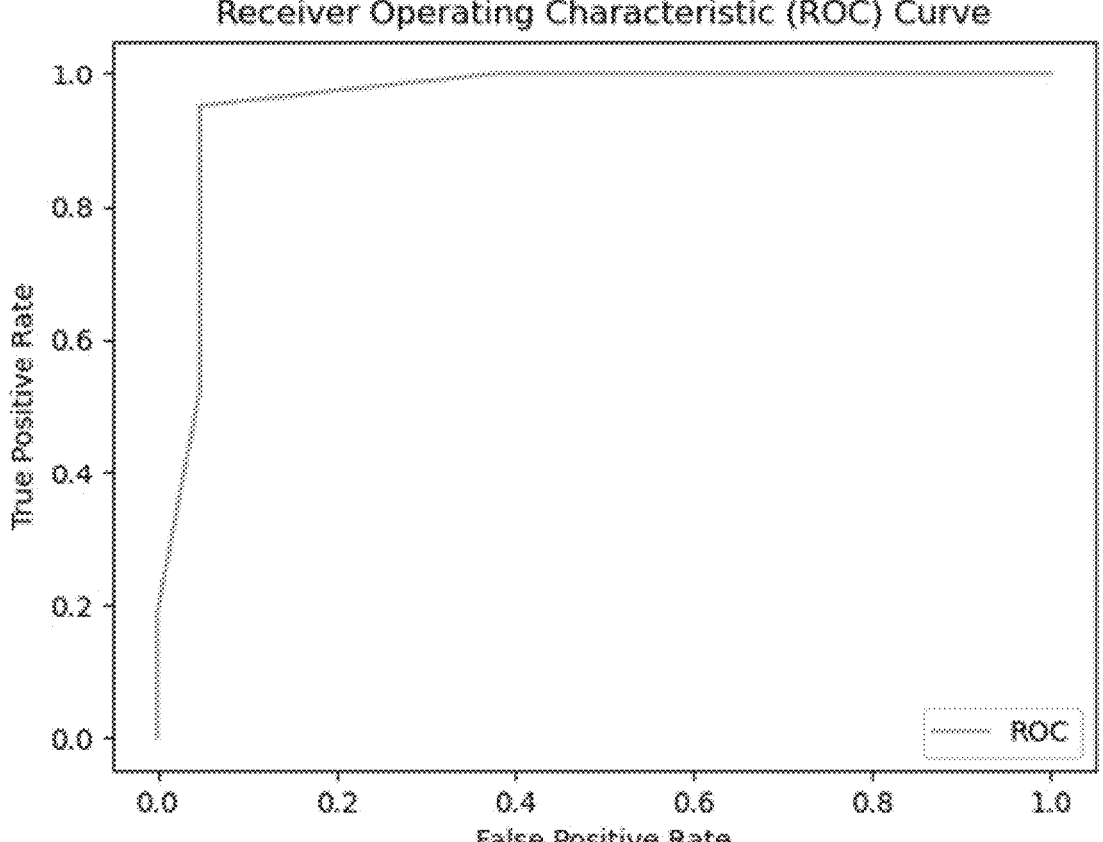
FIG. 19 is an ROC curve for the classification of strabismus and non-strabismus eyes using the CNN based strabismus detection method.

The trained model was validated with 21 images of strabismus and non strabismus images. The Receiver Operating Characteristic (ROC) curve of this classification is shown in FIG. 19. This method produced a True Positive Rate (TPR) of 95.23% and a False Positive rate (FPR) of 4.76%.

This embodiment of a method based on CNN has been developed for the detection of extreme strabismus eye images. The eye region is automatically segmented from the face image and is provided to trained VGG-16 CNN for the detection of the strabismus eye. This method can also be used in real-time, such as in step 226 in the method of FIG. 2, as the strabismus eye can be detected from every frame of the captured video. The detection accuracy of this method can be increased further by training the CNN with more images.

Measurement of Distance from Camera to Patient/Child

Prior to using the system and executing the method embodiment of FIG. 2, distance calibration of the camera is executed. This calibration can be part of the previously mentioned setup phase for the application. Measurement of distance from Camera to Patient/child is used to confirm that the patient is at correct testing/treatment distance. This is especially significant for stereopsis testing. In the present embodiments, face detection is used along with a triangular approach to estimate the distance of the face from the camera. As part of the distance calibration to find the focal length for the specific camera being used, a target of known width and length is placed at a known distance from the camera. The image of the target is taken and width of the image is estimated in terms of number of pixels. Then the focal length of the camera 'F' is obtained by the following equation.

$$F = (W\_i * D)/W\_p \qquad (15)$$

where Wi is the width of the image of the target, D is the known distance from the camera to the target, Wp is the width of the target in 'cm'. After calibration and when the system is executing the method embodiment of FIG. 2, the face is detected by haar cascade face detector. The distance from the camera to this detected face image is estimated in real time using the equation given below.

$$Distance = (W\_f * F)/W \qquad (16)$$

Where Wf image is the width of the image of the face in pixels, W is the actual width of the face. The average face width of a child is estimated as 5 cm and that adult is taken as 6.5 cm.

The digital therapy optimization method of FIG. 2 is an example of a closed-loop control mode of the system. In this mode the computed cues are used not only to assess attention, but also to assess any deviation from what is defined as proper attention and deduce behavioral compensation control strategies to mitigate such deviation. Sometimes the subject may be drowsy, multitasking with others or for some other reason not attending to the video during treatment and testing. The patient's wakefulness can be monitored by eye blink dynamics and yawning. Engagement of the patient in other activities (multi-tasking) during treatment or testing can be monitored by an analysis of head posture (face orientation) and eye gaze.

An example of use is in the treatment of Amblyopia, in which eye alignment is monitored. It is estimated that 60% of Amblyopia cases are associated with misaligned eyes. The described system of the present embodiment will allow, for the first time, real-time monitoring of this associated deficit and open the way to future "feedback" treatment directed specifically on either improving the eye-muscle balance in people without a manifest eye misalignment but with a large latent imbalance called a phoria or those with manifest eye-misalignments, either before or after surgical correction. Detected emotions like "sad" or "angry" also supply valuable information about whether the patient is feeling stressed by the therapy/testing or whether the patient is properly engaged with the therapy. The detected emotion of "happy" can be used to know that the patient is satisfied and comfortable undertaking the treatment/testing. Furthermore, using face recognition, the system can identify whether the right subject is receiving the treatment/testing, which is important since it is possible for siblings to have access to the treatment device.

Figure 20:
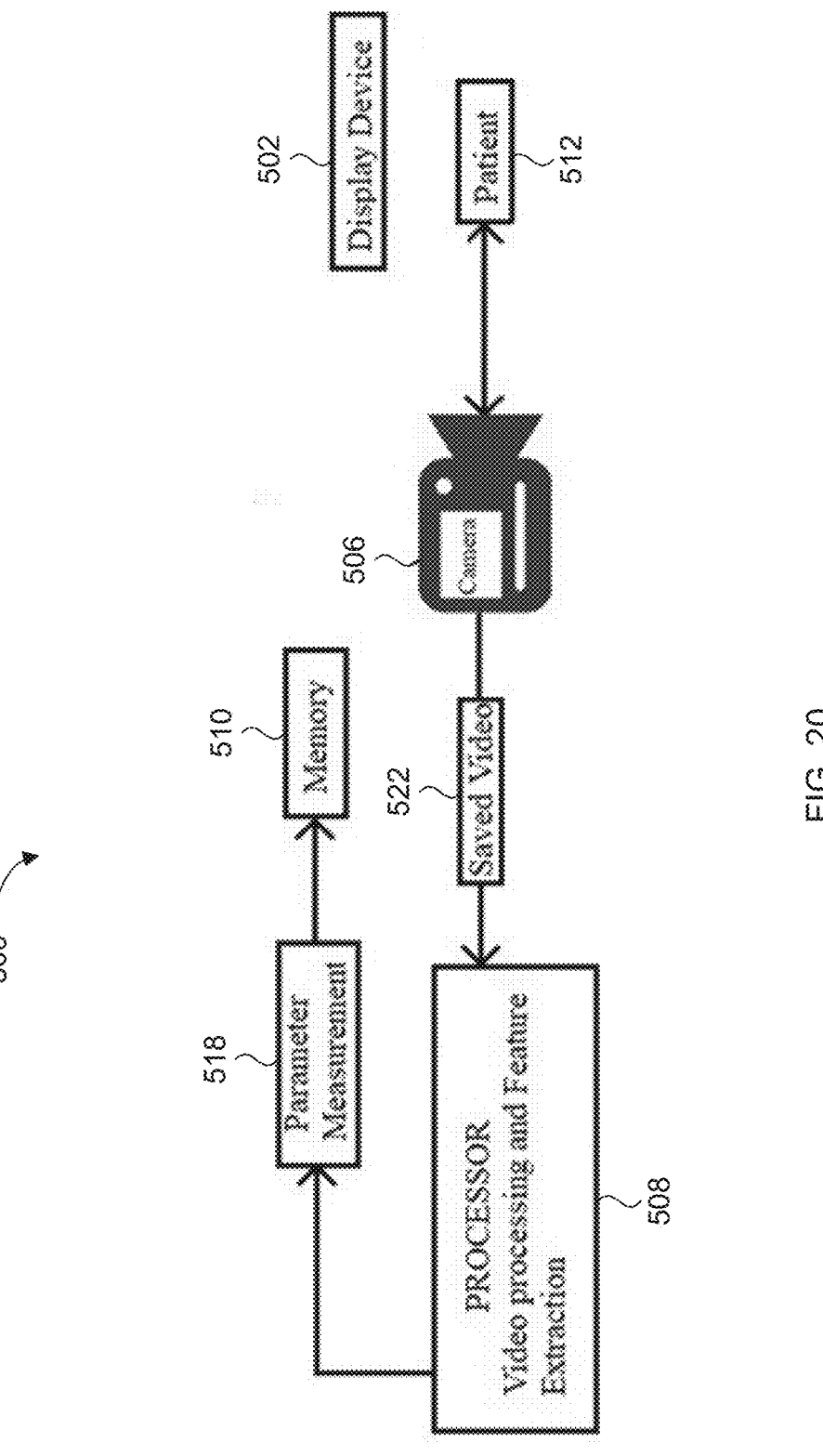
FIG. 20 is a block diagram of the digital therapy optimization system configured to operate in open loop mode, according to a present embodiment.

According to an alternate embodiment, the digital therapy optimization system 100 of FIG. 1 can be operated in open loop, or assessment and testing control mode. In this open loop control mode, the digital therapy optimization system 100 of FIG. 1 is configured as shown in FIG. 20 and referred to as the open loop adherence monitoring system 500. The open loop adherence monitoring system 500 includes a display device 502, an image capture device or camera 506, a processor 508, and a memory 510. These components can be the same as components 102, 106, 108 and 110 of FIG. 1, and the functional block for parameter measurement 518 executes the same detection algorithms as functional block 118 of FIG. 1.

One difference over the embodiment of FIG. 1 is that the system is configured to record and save the video frames captured by the camera 506 via the video saving functional block. These capture video frames can be saved to memory 510.

The system of FIG. 20 operating in open loop mode does not generate any feedback to the patient 512. Instead, the recorded video of the patient 512 engaging in a digital therapy or other human-device interaction can be analyzed in conjunction with the measured parameters as discussed below.

In this open loop mode, the system can be used to derive analytics that can quantify the level of attention and to perform attention level classification. In this mode the system can be used to achieve unsupervised machine-learning of the potential attention classes of subjects by experience. The system will be able to determine attention class prototypes and characterize each class in the feature space of the information cues computed by the system. Furthermore, the system can achieve supervised machine-learning of the attention classes by mapping the class definitions provided to it by an expert into its feature space. This allows the system to initiate its classification capabilities based on the supervised learning and discover other features to class mapping that were not identified by the expert.

The previously described embodiments are applied to treatment of vision problems in patients. According to an alternate embodiment, the digital therapy optimization system 100 of FIG. 1 and the corresponding digital therapy optimization method of FIG. 2 can be modified to provide a real-time online teaching adherence monitoring system. There are certain situations where teaching students in class is not possible due to specific conditions imposed by the environment, sociopolitical issues, personal issues etc. While modern computing systems and telecommunications systems provides the opportunity for remote/online learning by students with access to such technologies, similar issues to the ones described above for at-home treatment for vision problems in patients occur, namely attention to the content being presented by the teacher online. If the online class size is large, it becomes difficult for the teacher to monitor for adherence to the lesson while presenting and also it is difficult to assess how effective is their teaching material.

Here, online teaching is broadly construed to include primary, secondary and tertiary education along with continuing professional development training and employment related training such as health and safety training and certification. In this embodiment the same features are used to monitor the students and to send the alerts to the parents, supervisors, or teachers/instructors.

Figure 21:
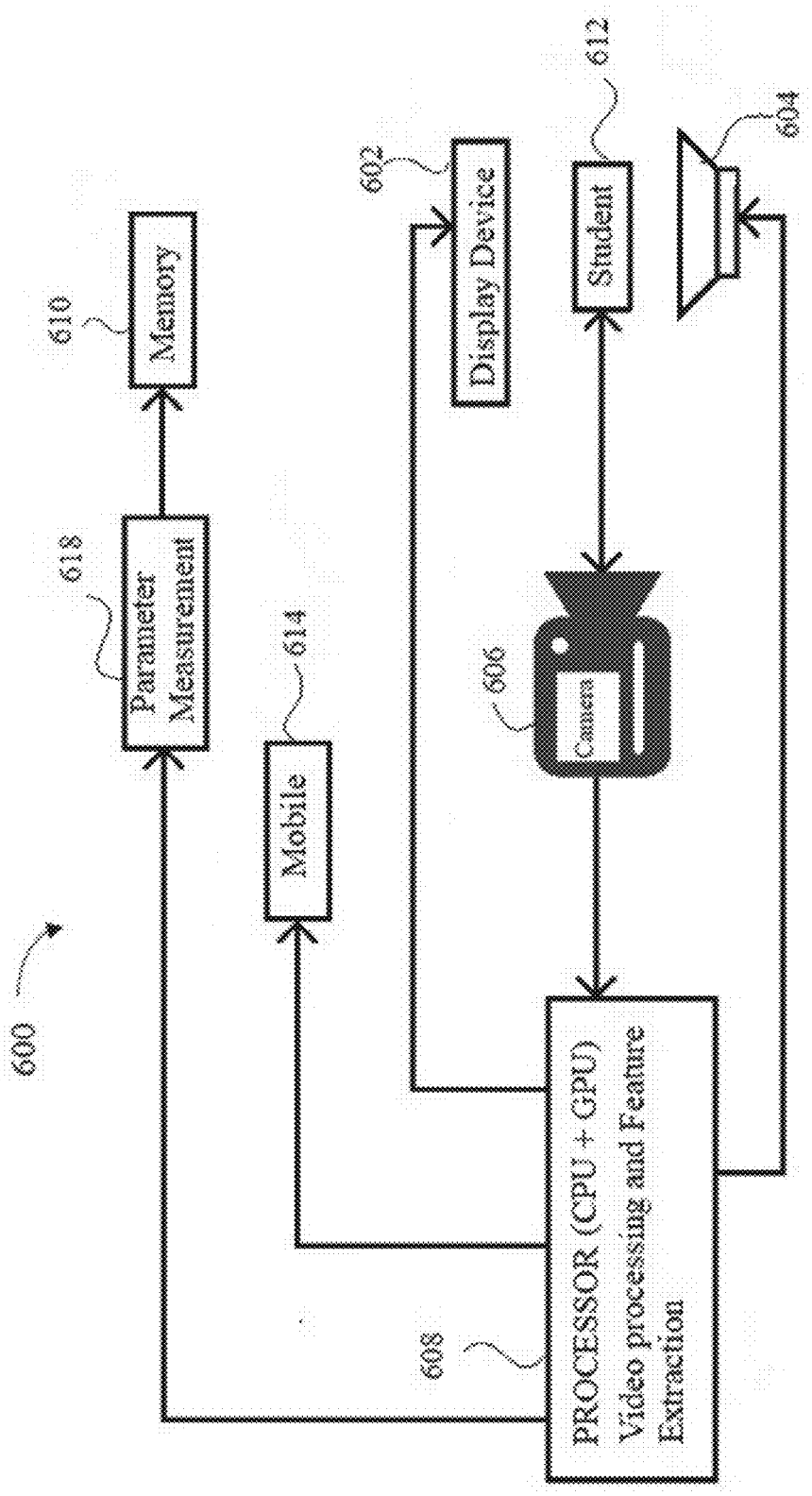
FIG. 21 is a block diagram of a real time monitoring system for online teaching, according to a present embodiment.

FIG. 21 is a diagram of a real-time online teaching adherence monitoring system 600 according to an alternate embodiment. System 600 is similar to system 100 shown in FIG. 1, and includes a display device 602, an audio output device 604, an image capture device or camera 606, at least one processor 608, a memory 610, and a mobile device 614. These components can be the same as components 102, 104, 106, 108 and 110 of FIG. 1, and the functional block for parameter measurement 618 executes the same detection algorithms as functional block 118 of FIG. 1. The mobile device 614 could be a handheld or laptop or computer in this alternate embodiment, in communication with the at least one processor 608 via well-known circuit elements for enabling wired or wireless communications.

In this alternate embodiment, the components shown in FIG. 21 can be integrated into a tablet, but can also be integrated in a laptop computer or as one or more peripheral devices of a desktop computer. For example, the system can be implemented with a Windows 10 PC that includes an Intel i7, $9^{th}$ generation processor and Nvidia Geforce GTX 1650 Ti GPU and a separate Logitech C920 video camera. Online teaching with software like zoom, Google meet, etc. can take place on the same PC by using its camera.

Additionally, instead of the patient there is a student 612 and there is no feedback system to manipulate the digital content on the display device 602. There is audio feedback using device 604 to regain the attention of the students, also allowing the teacher to talk to the student.

The digital therapy optimization method embodiment of FIG. 2 is easily adjusted for the system 600 in its use for real-time online teaching adherence monitoring. In particular, instead of eye-related parameter measurements and strabismus classification, time of drowsy state, time of effective engagement, and head stability are included in the measurements. In this adjustment of the method of FIG. 2, predetermined minimum thresholds can be set for the time of drowsy state, and time of effective engagement, which when detected from the student generates an alert to the teacher on their mobile device 614. The alert can include the name of the student and a short message that they are at least drowsy or not engaged. Similarly, a minimum predetermined threshold for head stability is set, and if the rate of change of head position of the student exceeds the minimum threshold, an alert is generated and sent to the mobile device 614 of the teacher indicating the student is likely doing something else other than paying attention to the display device 602. Similar thresholds to those used in the previous embodiments can be used here. In a variation of this embodiment, the teacher can set the thresholds based on their observations or experience with the set of students they are teaching online.

In another alternate embodiment, the digital therapy optimization system 100 of FIG. 1 and the corresponding digital therapy optimization method of FIG. 2 can be modified to provide a real-time driver fatigue monitoring system. This alternate embodiment provides a solution for driver fatigue monitoring in real time which uses the extracted features to detect fatigue and to provide feedback if fatigue is detected.

Figure 22:
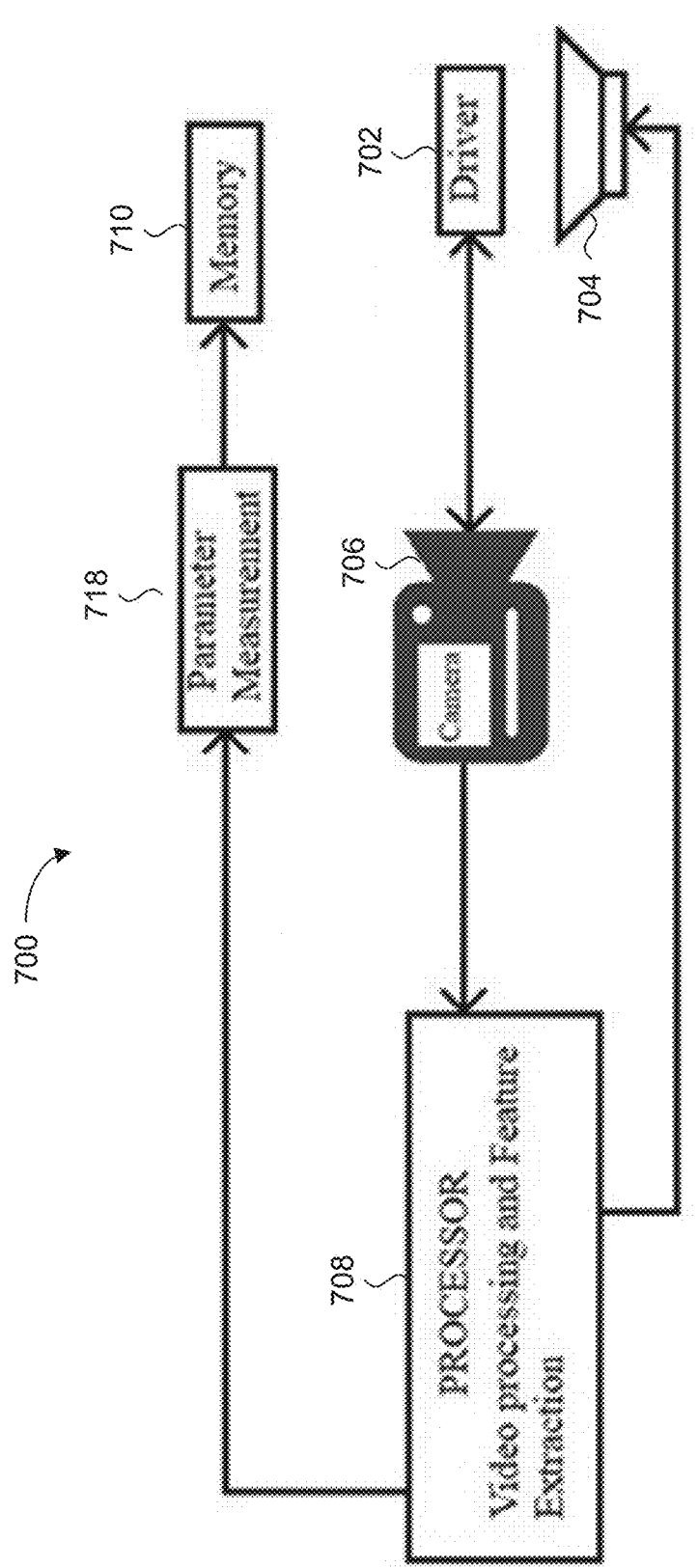
FIG. 22 is block diagram of a driver distraction monitoring system.

FIG. 22 is a diagram of a real-time driver distraction monitoring system 700 according to an alternate embodiment. System 700 has a subset of the components of the embodiment of FIG. 1, and includes a display device 702, an audio output device 704, an image capture device or camera 706, at least one processor 708 and a memory 710. These components can be the same as components 102, 104, 106, 108 and 110 of FIG. 1, and the functional block for parameter measurement 718 executes the same detection algorithms as functional block 118 of FIG. 1. Instead of a patient, there is now a driver of the vehicle 102. These components can be added to the driver side cabin of any vehicle and all that is required is connection to a power source and access to a user interface for initial set up.

The method of FIG. 2 is modified in this alternate embodiment to enable the drowsiness detection feature, while determining time of effective driving, eye gaze, emotional state, and head stability detection, the measured parameters of which are stored in memory 710. All of these parameters can be used to detect a distracted state of the driver. It is noted that in this embodiment of driver distraction detection, the head stability determination includes consideration of the roll parameter. As previously mentioned, the face is considered to be oriented straight, when the range of variation of these parameters in degrees are below fixed thresholds, for example $-5<=$pitch$<=10$, and $-20<=$yaw$<=20$, $-20<=$roll$<=20$. Therefore a detected head roll exceeding the roll limits is an indicator that the driver's head has lolled due to fatigue or drowsiness.

The time of effective driving differs from the total time of driving. The time of effective driving is determined as the aggregate time the driver is not detected as being in the drowsy state, not lacking head stability or eye stability, and as not having the previously discussed emergency emotional state. In the present embodiment, when any of the above criteria is detected for the predetermined time of 4 s, this time is subtracted from the current accumulated total time. If the running total effective driving time drops to some predetermined proportion relative to the total driving time, then a special audio alert can be generated for the driver. For example, it is possible the driver is progressively getting drowsier, so the special audio alert can be an alarm and/or audio message to pull over and rest.

In an alternate embodiment, the system determines effective time of driving in 5 minute blocks, and if the difference exceeds a predetermined threshold, then a special audio alert can be generated for the driver as described above. This predetermined threshold can be determined empirically, or set by the driver based on personal preference and/or trial and error. This feature can be combined with the above total elapsed effective driving time detection embodiment.

Figure 12:
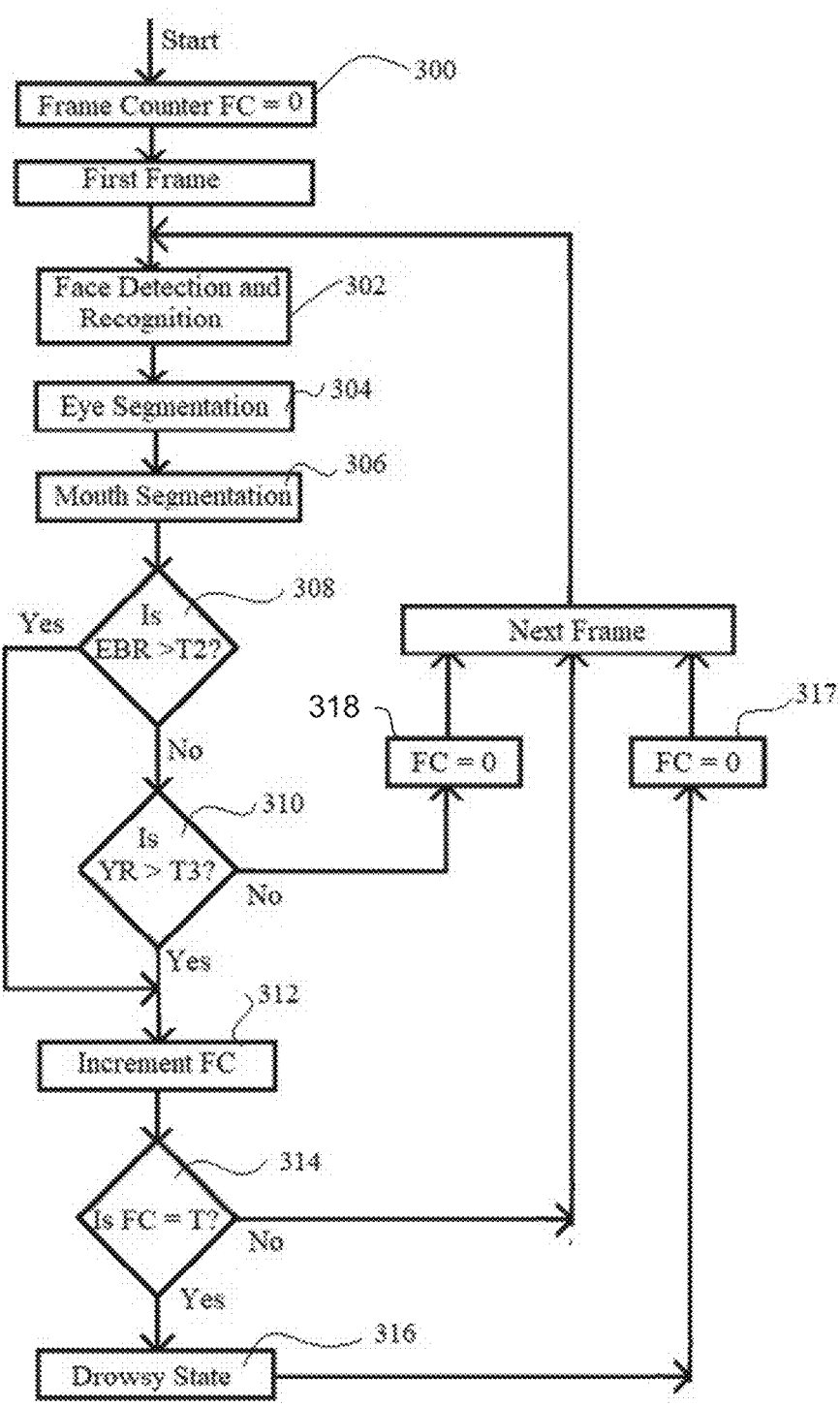
FIG. 12 is a flowchart of an algorithm for detecting a drowsy state of a person in a set of video frames, according to a present embodiment.

An algorithm for detecting a drowsy state of an individual that has been previously presented in FIG. 12, where two individual scores are generated for features of eye blinking rate (EBR) and yawn rate (YR), and these scores are combined together using OR fusion rule to detect the drowsy state. This same algorithm can be used in the real-time driver fatigue monitoring system 700.

Eye gaze and head stability are indicators of the location of the driver's eyes, which could be focused on the vehicle entertainment system, a mobile device or some other object other than straight in the direction of the vehicle for too long a duration of time (ie. 4 s), thereby indicating a distracted state of the driver. The driver could be staring in a direction that is clearly not within the straight direction of the vehicle, such as to the right or left side windows, which is also an indicator of a distracted state of the driver. However there may be situations where eye gaze is intentionally not staring within the straight direction of the vehicle for more than the preset duration of time, such as when the vehicle is at an intersection about to make a turn or at a required stop while the vehicle is not moving. Accordingly, such situations where an activated turn signal light is detected by the system, or a turning of the steering wheel beyond a predetermined threshold is detected by the system, can be used as an exception criterion to determine that the driver is not distracted when eye gaze is detected as not being straight. In alternate embodiments, the system can include an additional camera mounted to the front of the vehicle to detect turning and junctions for this purpose. Other detectable road conditions requiring the driver to gaze in directions other than straight can be taken into account as part of the present embodiment.

It has been well documented that emotional states affects/impairs driver performance. For example, if the driver is angry, they will have a tendency to increase driving speed and drive more erratically than when neutral or happy. It is also known that drivers who are in the sad emotional state also drive with riskier behaviors, thereby also affecting the safety of themselves and others. Since there are other emotional states which can affect driver performance, in an alternate embodiment, the system can detect the absence of the happy and neutral emotional states for at least the predetermined time (ie. 4 s), to capture emotional states other than angry and sad which can impact driver performance. The driver can be in, for example, a scared state, a disgusted state or a surprised state, which may not be detectable by the system as either angry or sad.

In summary, the modified method of FIG. 2 for system 700 uses the camera 706 to capture video frames of the driver 702, and if the system detects any drowsy state, lack of head stability or eye stability, and emotions (angry or sad) continuously for a predetermined threshold of 4 seconds, an audio alert is issued through the audio output device 704. For example this can be a prerecorded message to "wake up" if drowsiness is detected, or "please pay attention to the road ahead" if the detected head stability or eye stability is too low or "please be happy" if emotion is angry or sad.

In another variation of the embodiment of FIG. 22, many of the components shown can be integrated with an existing vehicle autonomous driving system with sensors and algorithms to automatically determine the outside environment of the vehicle and either provide semi or fully automatic control of the vehicle when certain conditions are detected. Most new vehicles sold have built-in displays and audio systems, hence the feedback mechanisms for the system are expanded to function similarly to the system of FIG. 1. Any detected inattentive or drowsy states of the driver during detected potential danger situations on the road can be used to increase the intensity or seriousness of an alert message. In a fully autonomous driving system, when drowsiness is detected and the alerts seem to have no effect on the driver, the driving system can take over and park the vehicle in a safe place until the driver returns to an alert state. Simultaneously, if the driving system has a wireless telecommunication system, it can send the message to an appropriate person(s) to advise them of the situation.

The previously described system and methods have been tested with actual patients. For the test, the system uses a modified video which is uploaded to Amazon AWS to access through a Nintendo 3DS device during the treatment. The system of the present embodiments measures eye stability, eye alignment stability, eye blinking rate, head stability, duration of attentive engagement, duration of general engagement, duration of treatment, and distance from the camera to the patient. Duration of engagement can be used to plan the treatment accordingly. Duration of attentive engagement is similar to time of effective driving discussed for the real-time driver distraction monitoring system embodiment.

The embodiments of the method and system for monitoring and optimizing human-device interactions were implemented and programmed for testing with children in a controlled laboratory setting, for the purposes of validating the effectiveness of the described system and method. The testing approach and results are now described.

The system uses modified video which is uploaded to Amazon AWS to access through the Nintendo 3DS device during the treatment. The proposed system measures eye stability, eye alignment stability, eye blinking rate, head stability, duration of attentive engagement, duration of general engagement, duration of treatment, and distance from the camera to the patient. Duration of engagement can be used to plan the treatment accordingly.

Figure 23:
FIG. 23 shows an example setup for recording video of a participant using the system and method of the present embodiments.

An analysis of 26 videos of children who watched animations modified for amblyopia treatment at the Crystal Charity Ball Paediatric Vision Laboratory, Retina Foundation of the Southwest were conducted. Videos of the children were recorded in a quiet room and the children watched the animations alone. The study was approved by the ethics committees of the University of Waterloo and the Retina Foundation of the Southwest. The animation videos that are specially designed for the binocular vision treatment of amblyopia are presented to each participant using a Nintendo 3DS XL gaming display as shown in FIG. 23. A Logitech C920 camera is mounted behind the screen to record the video into a laptop using Logitech capture software.

The age of children who participated in the study varied from 3 to 10 years. Children watched the videos with no control over their head or body posture (natural viewing) and each video had a duration of 10 minutes (the duration of the animation). The recorded video is given as input to the monitoring system, and it reads every frame one by one, processes it, and extracts the features needed for the estimation of time of engagement and other related parameters.

For the purposes of validating the system and method, the duration of engagement obtained by the real-time monitoring system was compared with the same estimated by manual analysis. This time duration is calculated by using eye gaze and head orientation. A counter f_GER is initialized with zero and it is incremented whenever the eye gaze is at the center and head orientation when 0<=(absolute value of pitch and yaw)<=25. After the end of the video, the time duration of engagement is calculated by $$DGE = (f\_GER/fps)/60$$

where "DGE" is the duration of general engagement and 'fps' is the number of frames per second. The head orientation is estimated by using three angles, pitch, yaw, and roll. As previously mentioned, the roll angle is not considered for finding the head orientation since there are situations where the children are still looking into the animation video even when the absolute value of the roll is high.

The duration of engagement is estimated manually as follows. Each video was manually analyzed and the number of seconds were counted when the eye gaze is at the left or right side and the head is not pointed in such a way that 0<=(absolute value of pitch and yaw angles)<=25. Then the duration of engagement 'MADGE' is calculated by subtracting the time estimated manually from the time duration of the treatment.

Independent student t-tests for comparing the duration of the engagement estimated by the real-time monitoring system and manual analysis were used. This test illustrates whether the duration of engagement estimated by the real-time system and the manual analysis is equal or not.

Figure 24:
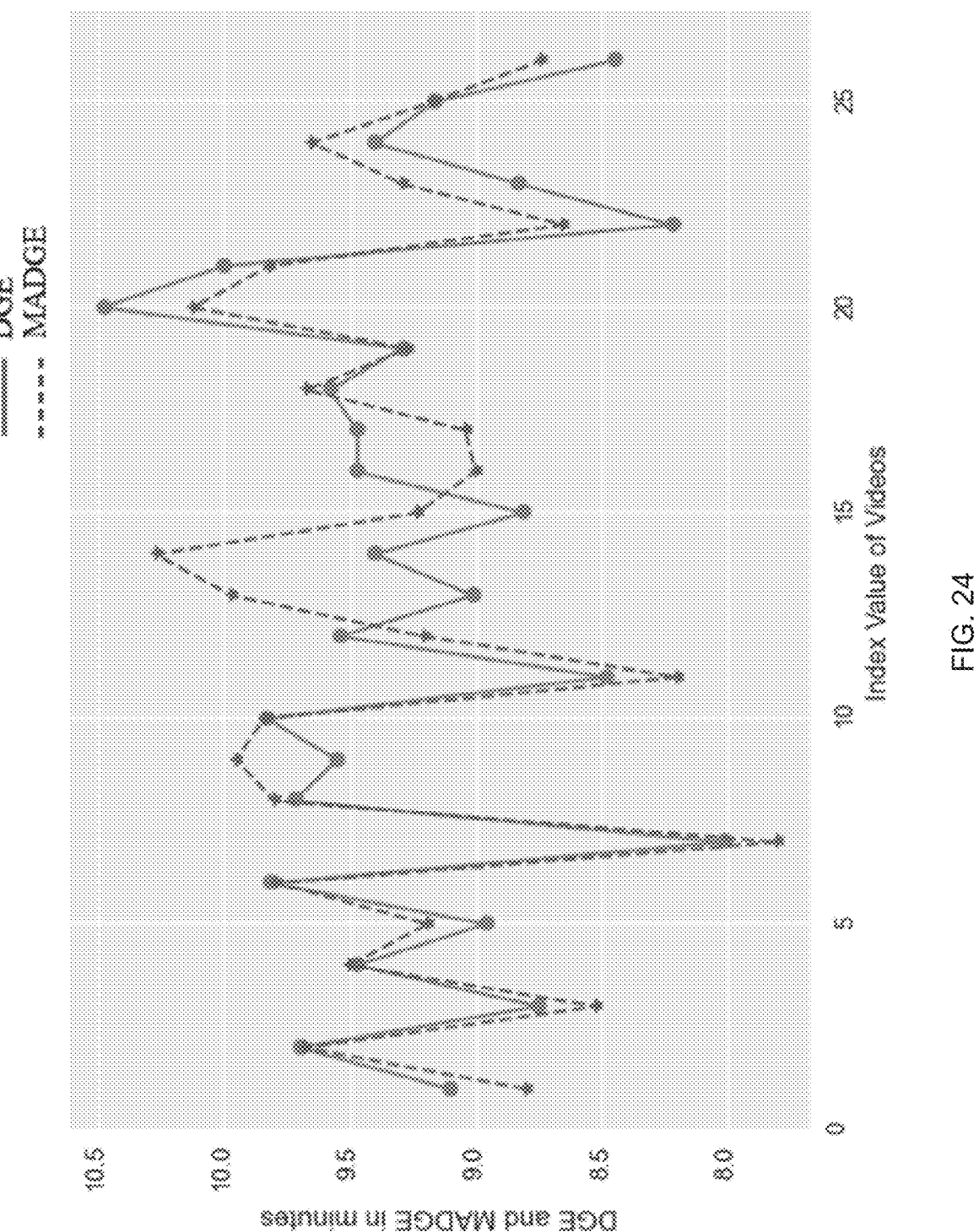
FIG. 24 is a plot of DGE and MADGE in minutes for 26 videos.

FIG. 24 shows the duration of general engagement obtained by the monitoring system as well as manual analysis. The Y axis shows the time in minutes and the X shows the index value of the videos.

Figure 25A:
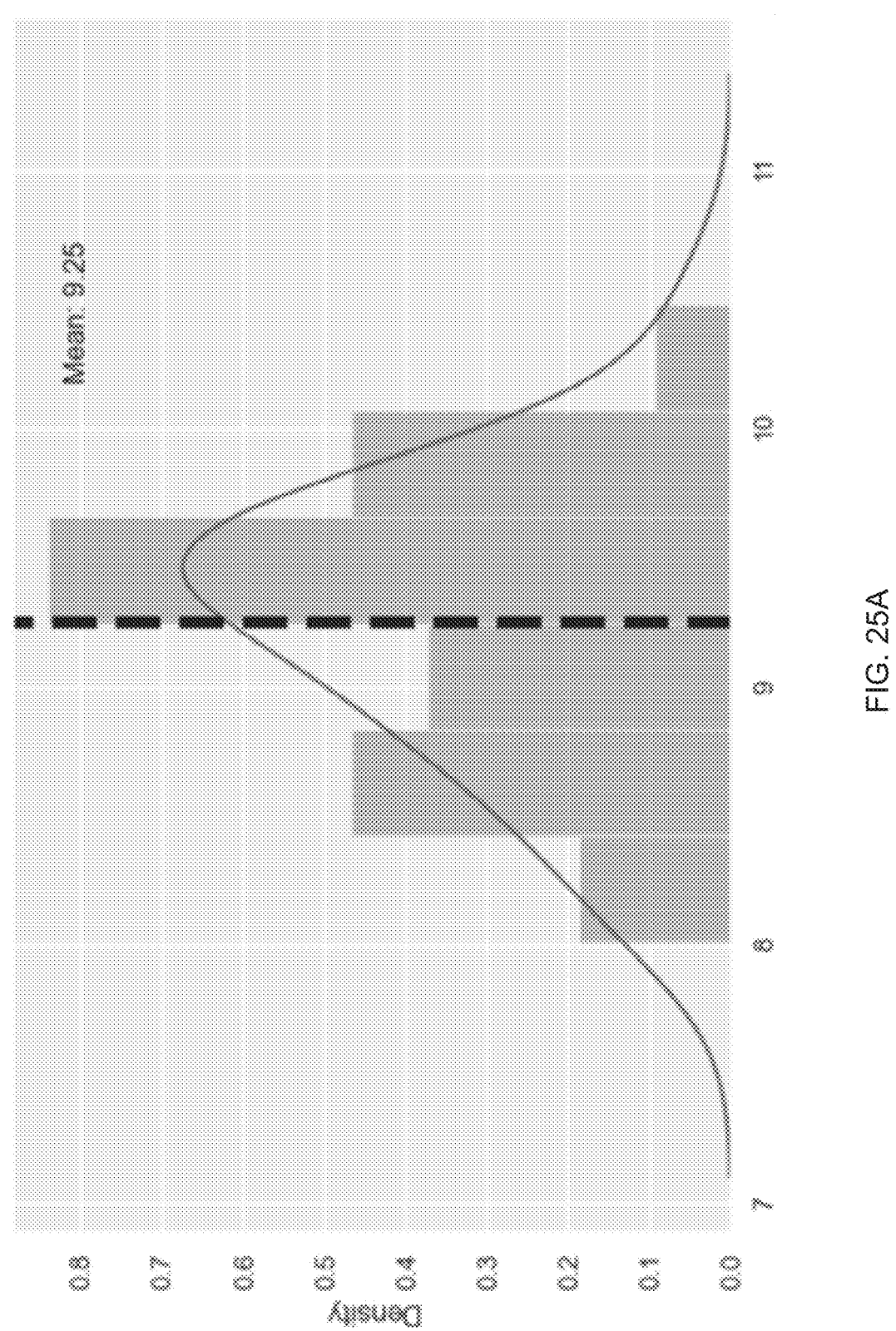
FIG. 25A is a plot of density distribution of general engagement measured by the monitoring system of the present embodiments.
Figure 25B:
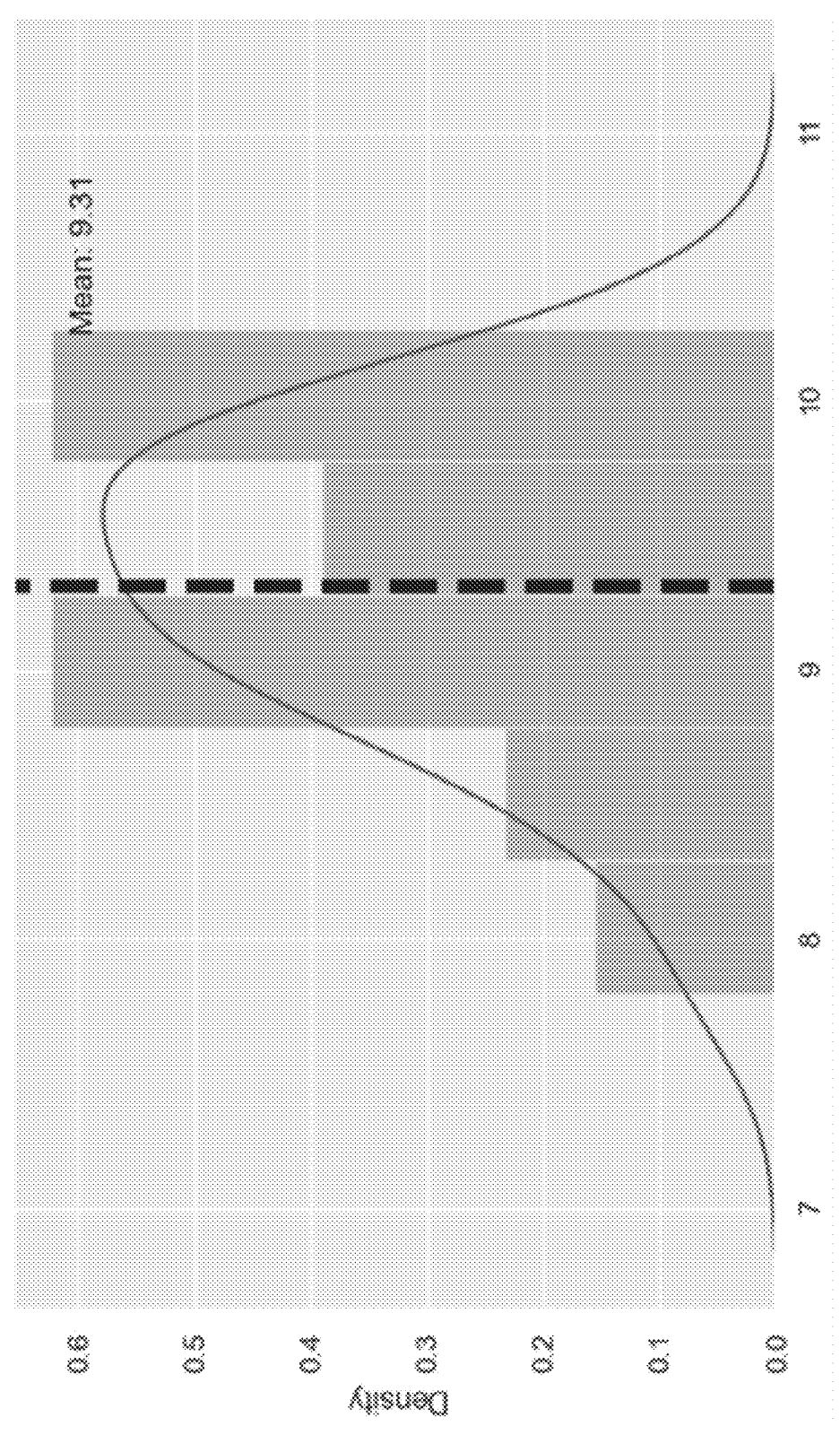
FIG. 25B is a plot of density distribution of general engagement measured by manual analysis.

DGE is concentrated on its mean at 9.25 and it varies between 8 and 10.5. FIG. 25B illustrates the distribution of general engagement obtained by manual analysis. The mean is 9.31.

Figure 26:
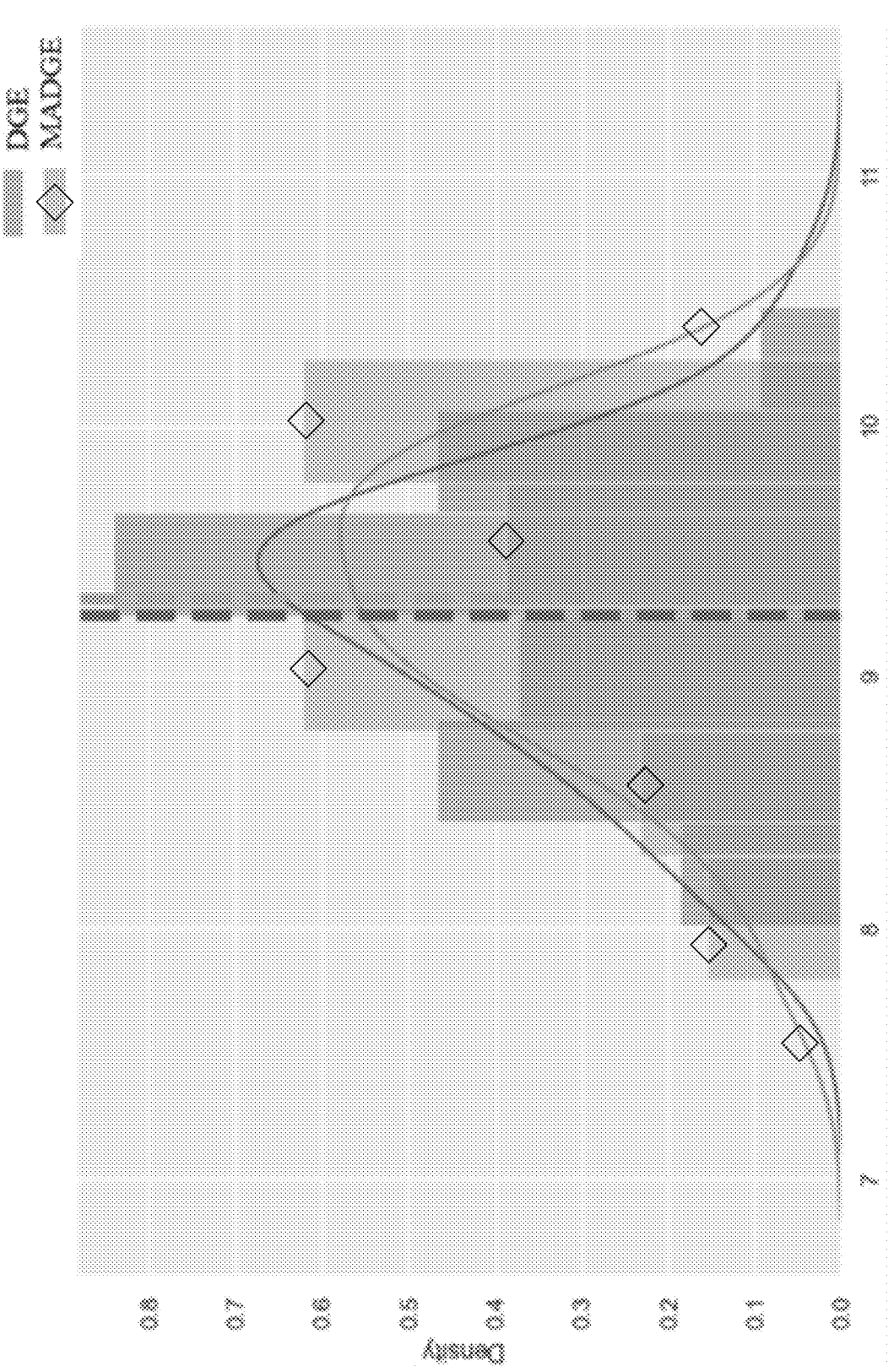
FIG. 26 is an overlay plot of density distribution of general engagement measured by manual analysis and by the monitoring system of the present embodiments.

FIG. 26 shows the plot of the density distribution of two parameters together in one graph and it is clear the difference between the means is small.

An independent t-test indicated no significant difference between the monitoring system and manual analysis, t=0.389 and p as 0.699. This shows that the two distributions are similar or in other words, the duration of general engagement measured by the algorithm and manual analysis of the video is the same.

Table 1 shows the parameters measured from 12 videos using the proposed real-time monitoring system. The percentages of eye stability shows how much time the eye gaze is concentrated at the center position, out of the total duration of the treatment so that the child can view the video. Similarly, head stability also gives the amount of time that the head pointed in a direction such that 0<=(absolute value of pitch and yaw angles)<=25. As can be seen in the table that the percentage of eye blinking (eye closure greater than 4 seconds) is small in all the videos, in fact almost equal to zero which shows that the eye blinking rate does not affect the duration of engagement of kids in the videos. Total eye stability is estimated by the weighted sum based fusion of eye blinking rate and eye stability. Its value mostly depends upon eye stability since more weight is given to this parameter. Attentive engagement is less than general engagement since it varies with eye gaze, head stability, and drowsy state while general engagement relies on eye gaze and head stability. Average eye alignment can be used for measuring the extreme cases of strabismus and it is detected when its value is greater than 10. In Table 1, the eye alignment is less than 10 and hence the participants do not have extreme strabismus. The average distance between the child and the camera is given in the table.

TABLE 1

| Parameters | 1 | 2 | 3 | 4 | 5 | 6 | 7 | 8 | 9 | 10 | 11 | 12 |
|---|---|---|---|---|---|---|---|---|---|---|---|---|
| Eye stability in (ES) in % | 85.6 | 99.0 | 93.3 | 87.3 | 88.2 | 87.3 | 83.9 | 92.5 | 100.0 | 99.8 | 68.5 | 95.4 |
| Head Stability in % | 98.8 | 99.4 | 92.5 | 98.7 | 100.0 | 99.6 | 93.5 | 97.0 | 99.5 | 98.9 | 90.2 | 96.7 |
| Eye Blinking in % | 0.3 | 0.5 | 0.6 | 0.1 | 0.0 | 0.0 | 0.0 | 0.3 | 0.0 | 0.02 | 0.1 | 0.0 |
| Total Eye Stability in % | 77.1 | 98.1 | 85.9 | 78.6 | 79.4 | 78.6 | 75.5 | 83.2 | 97.8 | 96.6 | 61.7 | 85.8 |
| Attentive Engagement in % | 89.1 | 97.2 | 75.0 | 97.2 | 87.3 | 97.8 | 92.0 | 95.2 | 95.7 | 98.2 | 84.1 | 96.3 |
| General Engagement in % | 91.1 | 97.9 | 87.5 | 97.3 | 94.7 | 98.2 | 92.5 | 95.9 | 95.7 | 98.2 | 85.1 | 96.3 |
| Average eye alignment stability | 1.7 | 1.0 | 0.7 | 0.8 | 3.4 | 1.4 | 0.6 | 0.9 | 1.7 | 1.1 | 1.2 | 1.6 |
| Avg. distance from camera to patient in cm | 13.1 | 16.6 | 16.6 | 18.8 | 15.5 | 16.6 | 18.6 | 16.2 | 20.6 | 17.1 | 15.6 | 17.3 |

Both parameters vary in a similar fashion and variation ranges between 8 and 10.5. The density distribution of both the parameters were plotted and FIG. 25A shows the density distribution of the duration of general engagement measured by the monitoring system and it's mean. The distribution of For the illustration of the variation of parameters along the full length of the video, two videos were selected of the participants that have excellent engagement and low engagement. Looking at Table 1, videos 10 and 11 have excellent engagement and low engagement respectively.

Figure 27A:
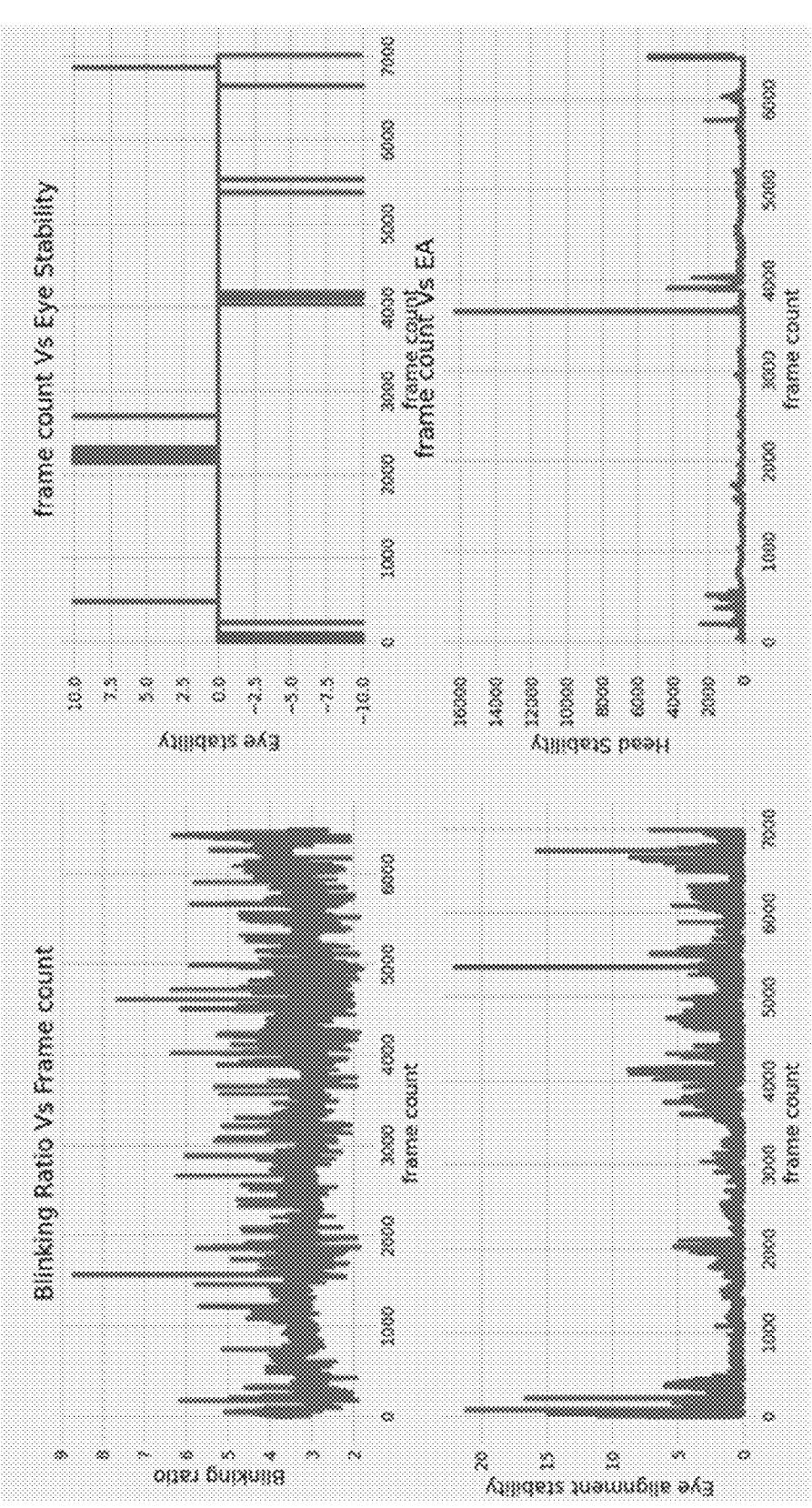
FIG. 27A are graphs showing parameters of blinking ratio, eye alignment stability, eye stability, and head stability measured from a first video plotted with respect to frame count.
Figure 27B:
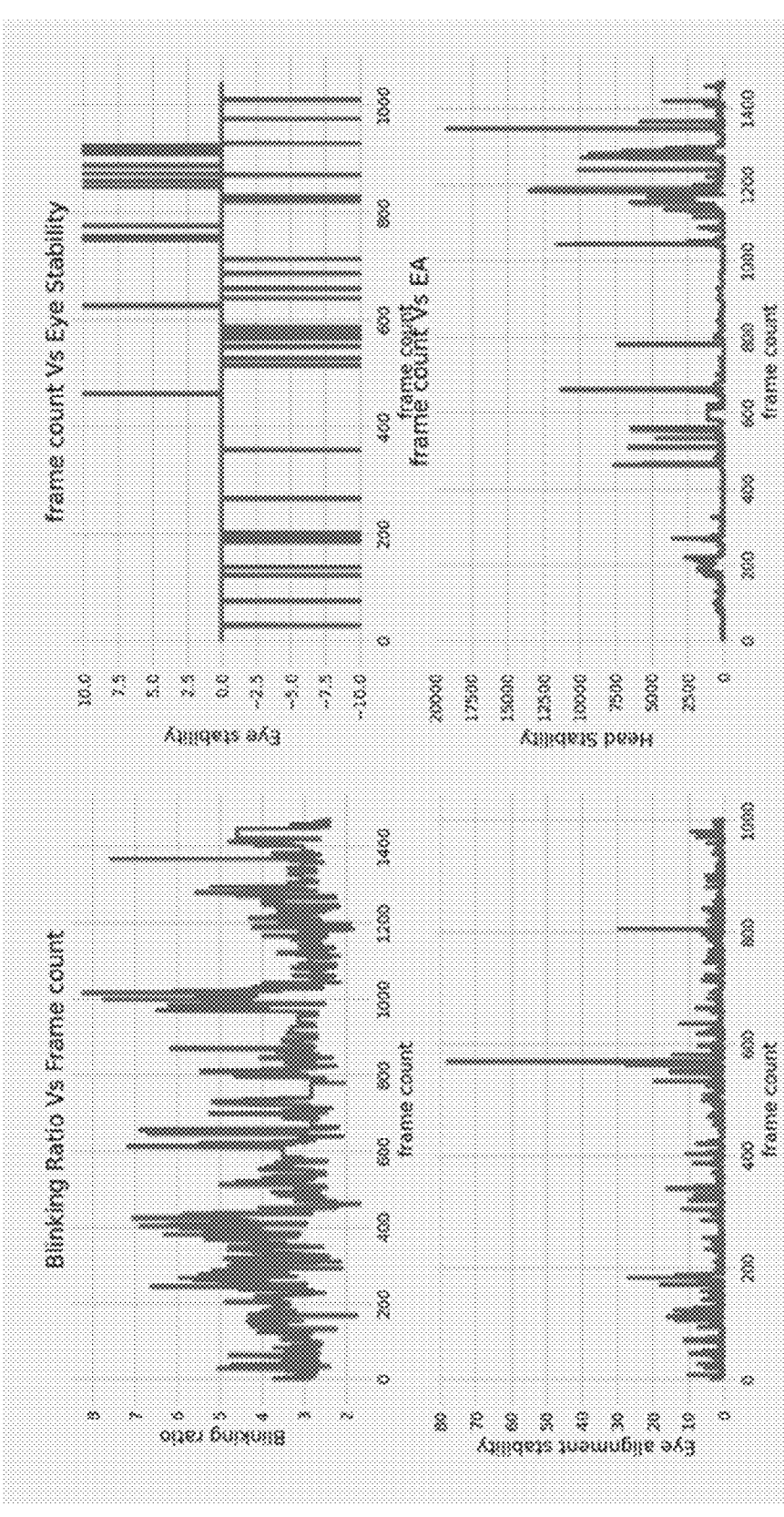
FIG. 27B are graphs showing parameters of blinking ratio, eye alignment stability, eye stability, and head stability measured from a second video plotted with respect to frame count.

It has already been noted from Table 1 that the child in video 10 has more engagement duration than that in video 11. FIGS. 27A and 27B give the evidence for this statement. FIG. 27A are graphs showing parameters (blinking ratio, eye alignment stability, eye stability, and head stability) measured from video 10 plotted with respect to frame count. FIG. 27B are graphs showing parameters (blinking ratio, eye alignment stability, eye stability, and head stability) measured from video 11 plotted with respect to frame count.

The blinking ratio in the graph shown in FIG. 27B has gone beyond its threshold more times than that of FIG. 27A. Thus the number of occurrences of eye blinking is higher in video 11 as compared to video 10. The value of eye stability is 10, 0, and −10 when the eye gaze moves to the right side, center, and left side respectively. This gives the information about what extent the eyes of the subject are stable or targeting the digital material that has been presented for the treatment. From the graph in FIG. 27B, it is clear that the eye gaze is at the left or right side more times than that of FIG. 27A or the eye gaze is more stable in video 10 as compared to that of video 11. The head is rotated more than 250 when head stability is greater than a threshold value of 625. Head stability is directly proportional to the absolute value of EA which is the product of two angles. This product sometimes goes higher and hence the head stability also goes beyond 1000. When the head turns more, the value of EA also increases accordingly. It is clear from that the head is more stable in video 10 as compared to that in video 11. Similarly, the value of average eye alignment stability in video 11 is higher as compared to that of video 10.

Figure 28A:
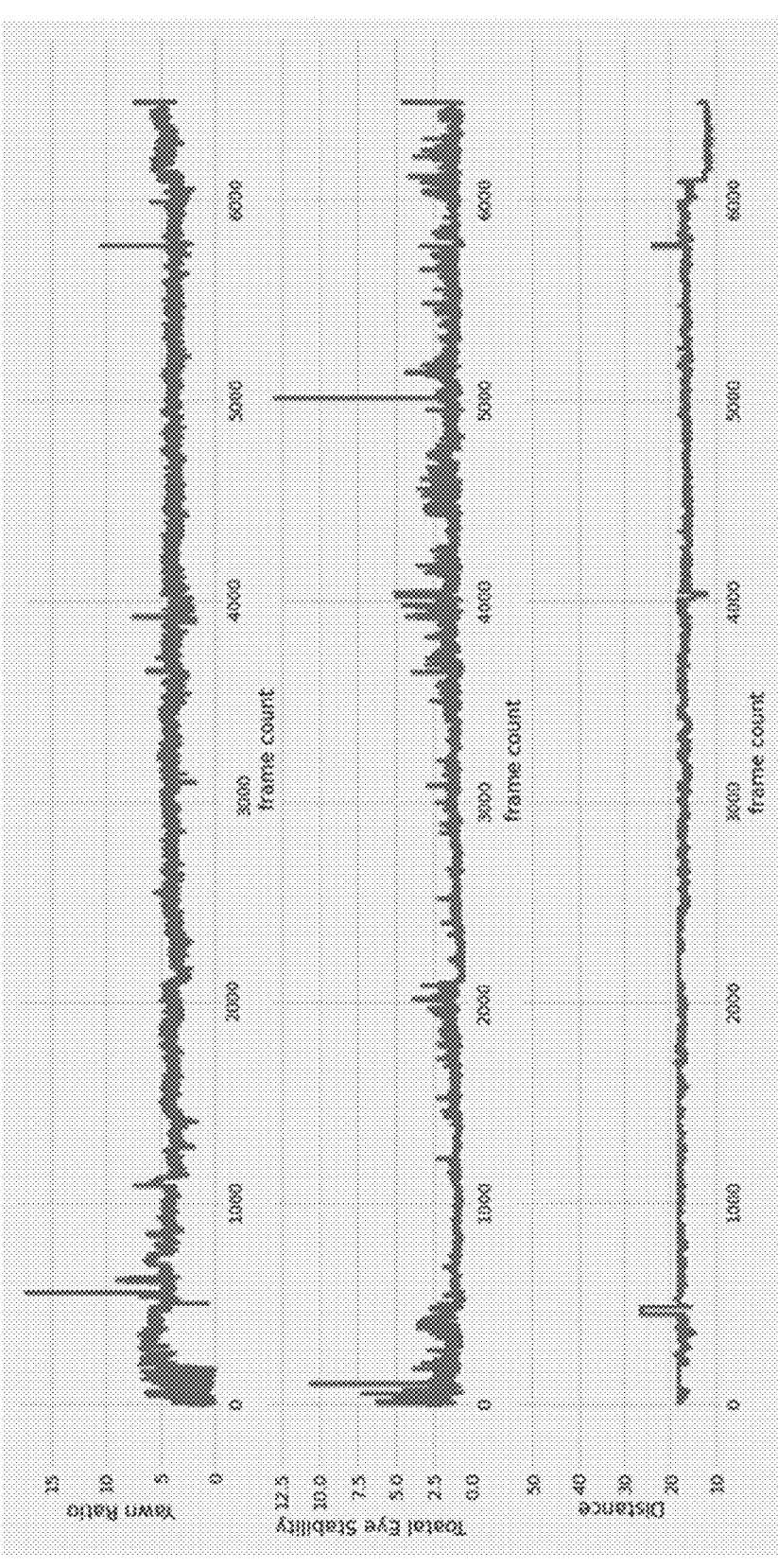
FIG. 28A are graphs showing parameters of yawn ratio, total eye stability and distance measured from the first video plotted with respect to frame count.
Figure 28B:
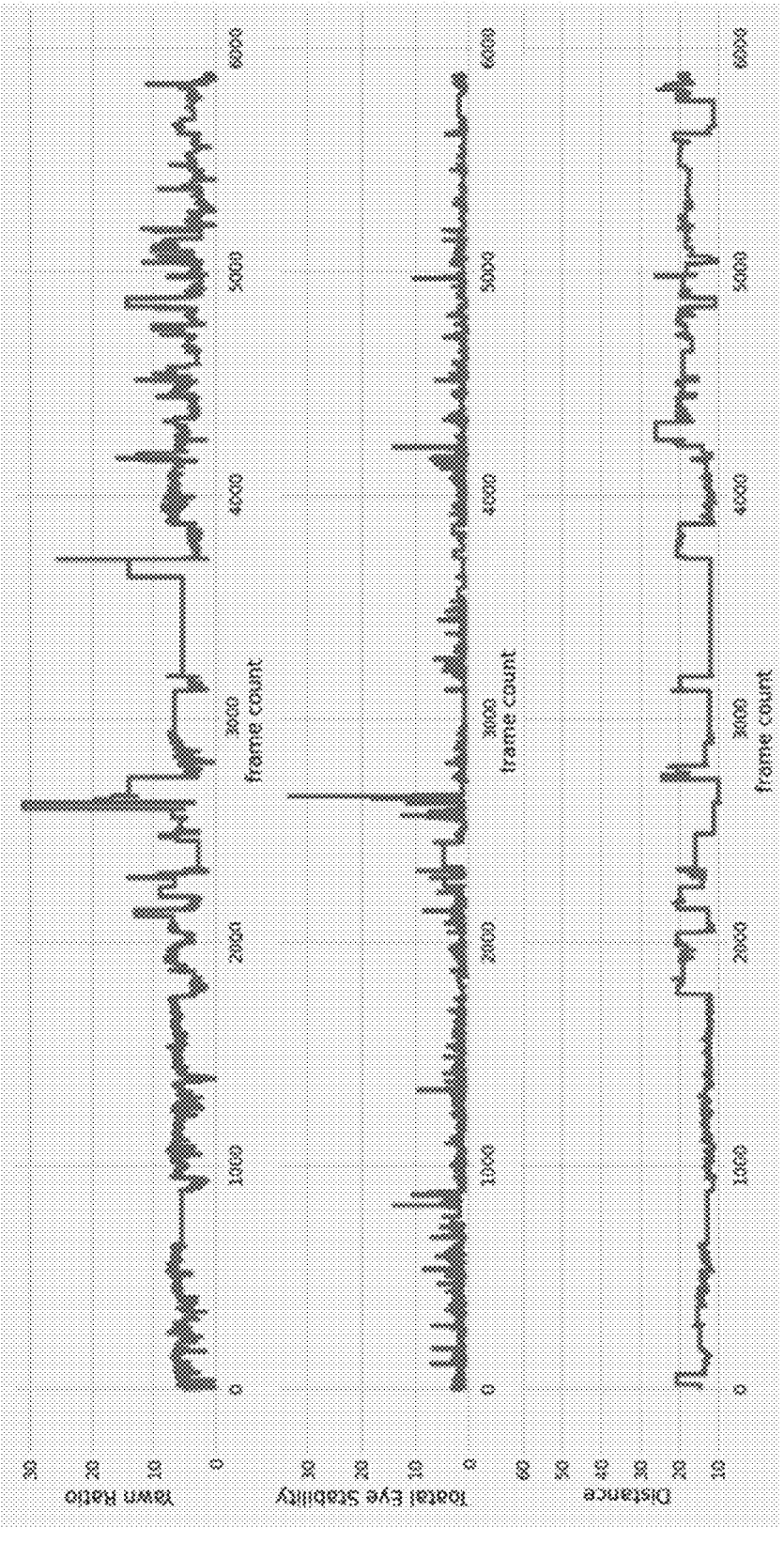
FIG. 28B are graphs showing parameters of yawn ratio, total eye stability and distance measured from the second video plotted with respect to frame count.

FIG. 28A are graphs showing parameters (yawn ratio, total eye stability and distance) measured from video 10 plotted with respect to frame count. FIG. 28B are graphs showing parameters (yawn ratio, total eye stability and distance) measured from video 11 plotted with respect to frame count. The yawning ratio, total eye stability, and distance between the child and camera also vary randomly along the whole length of the video in FIG. 2 as compared to that in FIG. 28A. For example, if we examine the distance in case of video 11 shown in FIG. 2 is not constant through the whole length of the video and it indicates that the child is regularly moving back and forth. The time of engagement depends upon all these parameters and is, in turn, the reason for the low engagement of the child in video 11 as compared to video 10.

The test results above illustrate that the monitoring system according to the present embodiments can be used in real-time as well as to analyze the recorded videos of the patient engaged in the treatment of amblyopia. The patient is required to view the specially created animation video of 10 minutes presented through the digital display device. The system uses a camera to capture the video of the patient in real-time and extracts visual cues from each frame of the video. These visual cues are used to provide feedback to the patient using a Finite State Machine consisting of three states whenever the attention of the patient is distracted. The system is able to measure the eye-related parameters as well as other parameters to decide the time of engagement. It is validated with 26 recorded videos of the kids who participated in the treatment. The effective time of engagement measured by the system is compared with a manually estimated time of engagement using an independent t-test. The test shows that the results are not significantly different.

Figure 29:
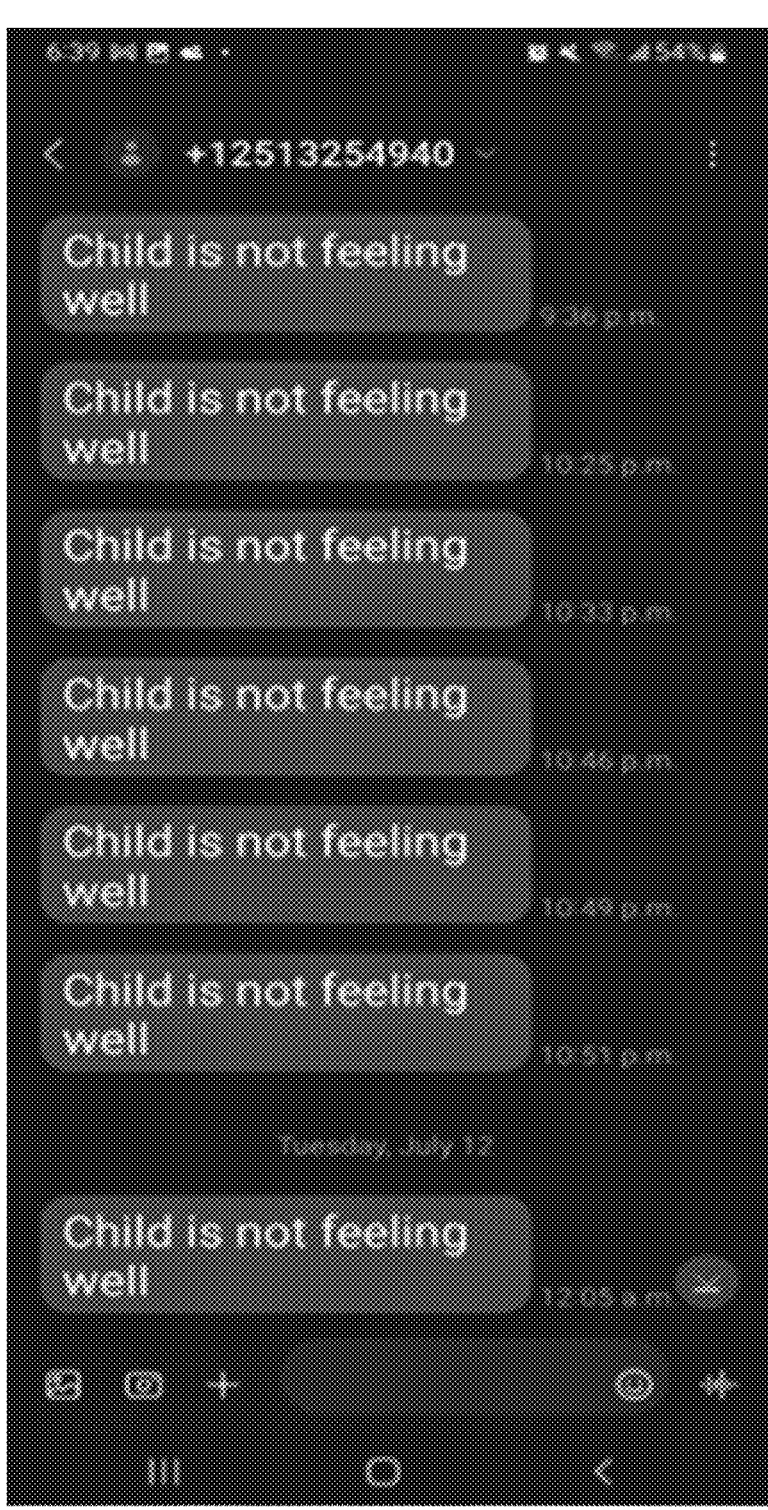
FIG. 29 is a screen shot showing example feedback provided to a mobile device when an emotional state (State III) of the child is detected.

The effective time of engagement estimated from these videos depends more on head stability and eye stability since the number of times the drowsy states are detected is less. F or these recorded videos, the feedback is working, and the system is also able to provide feedback to both the patient and the instructor. In the test, a feedback is provided to a mobile device indicating the emotional state (State III) of the child as detected by the system of the present embodiments. An example screen shot of a mobile receiving such feedback/notifications appears in FIG. 29.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

Embodiments of the disclosure can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

The invention claimed is:

1. A system for detecting an inattentive state of a person, comprising:
   a video game system including a controller to provide user input and an electronic display at which a person's eyes are directed at configured to present a video game for viewing and playing by the person;
   an image capture device positioned to capture digital video frames of the person's head and face;
   a computing device configured to receive the captured digital video frames and extract visual cues of eyes and mouth of the person's head and face from each of the captured digital video frames, the computing device further configured to
   increment a frame counter when
   an average of an aspect ratio of a left eye and a right eye of the person exceeds a predetermined threshold in a current video frame, or
   a yawn is detected from the shape of the mouth in the current video frame and the average of the aspect ratio of the left eye and the right eye of the person is less than or equal to the predetermined threshold, reset the frame counter when no yawn is detected in the current video frame, generate a first electronic signal when the frame counter reaches a predetermined number of frames and resetting the frame counter;

the computing device is further configured to detect an eye gaze of the person is to the left or to the right of the screen by extracting the eye portions from the face in the current video frame, determining a first ratio of white pixels corresponding to the right side and the left side of the left iris, determining a second ratio of white pixels corresponding to the right side and the left side of the right iris, determining the eye gaze is to the right when an average of the first and second ratios is below a first eye gaze threshold, determining the eye gaze is to the left when the average is greater than a second eye gaze threshold, and determining the eye gaze is centered when the average is between the first and second eye gaze thresholds, and the computing device generates a second electronic signal when the eye gaze is determined as being to the right or the left, wherein the computing device is configured to change currently displayed content of the electronic display device in real time to display new content non-native to the video game in response to at least one of the first and the second electronic signals, indicating the inattentive state of the person.

2. The system of claim 1, further including an audio output device controlled by the computing device to generate an audio alert when at least one of the first and the second electronic signals is received.

3. The system of claim 1, wherein the computing device is configured to detect from the captured video frames the at least one visual cue of emotional state of the person as being one of happy, neutral, sad or angry.

4. The system of claim 3, wherein when the computing device detects either the sad or angry emotional states, the computing device controls the audio output device to provide an indication of an emergency state of the person.

5. The system of claim 4, wherein the computing device generates and transmits an alert to a mobile device of another person in response to the detected emergency state of the person.

6. The system of claim 1, wherein the computing device is configured to determine a left eye alignment as a first ratio of a number of left side white pixels to a number of right side white pixels of the left eye of the person, a right eye alignment as a second ratio of a number of left side white pixels to a number of right side white pixels of the right eye of the person, eye alignment stability as the absolute value of the ratio of the left eye alignment to the right eye alignment, and a classification of the eye alignment stability greater than a predetermined threshold and generating an output indicating the person exhibits strabismus.

7. The system of claim 1, wherein the computing device is configured to determine strabismus from a video frame as input to a convolution neural network trained with eye regions segmented from 175 each strabismus and non-strabismus eye images, with at least specifications of an epoch of 600, batch size of 32, and image size of 100×100.

8. The system of claim 1, wherein the new content non-native to the video game includes a graphic overlay on presented content of the video game on the electronic display.

9. The system of claim 1, wherein the new content non-native to the video game includes changing to a different video game.

10. The system of claim 1, further including pausing the video game in response to the at least one of the first and the second electronic signals.

11. The system of claim 1, further including to changing a difficulty level of the video game in response to the at least one of the first and the second electronic signals.

12. A system for detecting an inattentive state of a person driving an automobile equipped with an autonomous driving system, comprising:

a windshield of a vehicle at which a person's eyes are directed at;

an audio output device;

an image capture device positioned to capture digital video frames of the person's head and face;

a computing device configured to receive the captured digital video frames and extract visual cues of eyes and mouth of the person's head and face from each of the captured digital video frames, the computing device further configured to a) increment a frame counter when an average of an aspect ratio of a left eye and a right eye of the person exceeds a predetermined threshold in a current video frame, or a yawn is detected from the shape of the mouth in the current video frame and the average of the aspect ratio of the left eye and the right eye of the person is less than or equal to the predetermined threshold, b) reset the frame counter when no yawn is detected in the current video frame, c) generate a first electronic signal indicating a drowsy state of the person when the frame counter reaches a predetermined number of frames and resetting the frame counter; and d) generate an audio alert to change the drowsy state of the person to an alert state, and repeating steps a) through c) in response to the first electronic signal, wherein when the drowsy state of the person is still detected after audio alert is generated the computing device is configured to control the autonomous driving system to take over control of the automobile and park the automobile in a safe area.

13. The system of claim 12, wherein the computing device is configured to determine pitch and yaw of the head of the person from the current video frame, and to determine that the head of the person is oriented straight when the determined pitch and yaw are within corresponding predetermined orientation thresholds.

14. The system of claim 13, wherein the computing device is configured to determine proper head stability of the person when a ratio of a number of frames with the person's head oriented straight towards the windshield to the total number of frames captured over a predetermined period of time exceeds a predetermined head stability threshold.

15. The system of claim 14, wherein the computing device is configured to control the audio output device to generate the audio alert in response to any one of the detected drowsy state of the person and when the head stability of the driver falls below the predetermined head stability threshold.

16. The system of claim 12, wherein the computing device is further configured to detect an eye gaze of the person is to the left or to the right of the screen by extracting the eye portions from the face in the current video frame, determining a first ratio of white pixels corresponding to the right side and the left side of the left iris, determining a second ratio of white pixels corresponding to the right side and the left side of the right iris, determining the eye gaze is to the right when an average of the first and second ratios is below a first eye gaze threshold, determining the eye gaze is to the left when the average is greater than a second eye gaze threshold, and determining the eye gaze is centered when the average is between the first and second eye gaze thresholds, and the computing device is configured to generate a second electronic signal indicating a distracted state of the driver when the eye gaze is determined as being to the right or the left for a predetermined duration of time, and the audio device is controlled to generate another audio alert in response to the second electronic signal.

\* \* \* \* \*